United States Patent
Yeh et al.

(10) Patent No.: US 10,407,715 B2
(45) Date of Patent: Sep. 10, 2019

(54) METAL NANOCLUSTER BEACONS FOR DETECTION OF EPIGENTIC MODIFICATIONS

(71) Applicant: BOARD OF REGENTS, THE UNIVERSITY OF TEXAS SYSTEM, Austin, TX (US)

(72) Inventors: Hsin-Chih Yeh, Austin, TX (US); Judy M. Obliosca, Austin, TX (US); Yu-An Chen, Austin, TX (US); Cong Liu, Austin, TX (US); Yen-Liang Liu, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 269 days.

(21) Appl. No.: 15/231,262

(22) Filed: Aug. 8, 2016

(65) Prior Publication Data
US 2017/0037455 A1 Feb. 9, 2017

Related U.S. Application Data

(60) Provisional application No. 62/202,424, filed on Aug. 7, 2015.

(51) Int. Cl.
| | | |
|---|---|---|
| C12Q 1/68 | (2018.01) | |
| C07H 21/00 | (2006.01) | |
| C12Q 1/6818 | (2018.01) | |
| C12Q 1/6816 | (2018.01) | |

(52) U.S. Cl.
CPC ......... *C12Q 1/6818* (2013.01); *C12Q 1/6816* (2013.01)

(58) Field of Classification Search
CPC .................................. C12Q 1/68; C07H 21/00
See application file for complete search history.

(56) References Cited

U.S. PATENT DOCUMENTS

| | | | | |
|---|---|---|---|---|
| 8,476,014 | B2 * | 7/2013 | Yeh ...................... | C12Q 1/6816 435/6.1 |
| 9,499,866 | B2 * | 11/2016 | Yeh ...................... | C12Q 1/6881 |
| 2006/0051878 | A1 * | 3/2006 | Dickson ................ | B82Y 15/00 436/518 |
| 2008/0118912 | A1 * | 5/2008 | Dickson ............. | A61K 49/0065 435/6.12 |

OTHER PUBLICATIONS

Handy et al., Circulation123 (19) : 2145 (Year: 2011).*
Ma et al., Nanotechnology 22 : 305502 (6pp) (Year: 2011).*
Yeh et al., Nano Letters 10 :3106 (Year: 2010).*
Chen, Yu-An, et al. "NanoCluster Beacons Enable Detection of a Single N 6-Methyladenine." *Journal of the American Chemical Society* 137.33 (2015): 10476-10479.
Dai, Qing, et al. "Identification of recognition residues for ligation-based detection and quantitation of pseudouridine and N6-methyladenosine." *Nucleic acids research* 35.18 (2007): 6322-6329.
Dominissini, Dan, et al. "Transcriptome-wide snapping of N6-methyladenosine by m6A-seq based on immnunocapturing and massively parallel sequencing." *Nature protocols* 8.1 (2013): 176-189.
Juul, Sissel, et al. "NanoCluster Beacons as reporter probes in rolling circle enhanced enzyme activity detection." *Nanoscale* 7.18 (2015): 8332-8337.
Meyer, Kate D., and Samie R. Jaffrey. "The dynamic epitranscriptome: N6-methyladenosine and gene expression control." *Nature Reviews Molecular Cell Biology* 15.5 (2014): 313-326.
Obliosca, Judy M., Cong Liu, and Hsin-Chih Yeh. "Fluorescent silver nanoclusters as DNA probes." *Nanoscale* 5.18 (2013): 8443-8461.
Obliosca, Judy M., et al. "A complementary palette of NanoCluster Beacons." *ACS nano* 8.10 (2014): 10150-10160.
Obliosca, Judy M., et al. "DNA/RNA detection using DNA-templated few-atom silver nanoclusters." *Biosensors* 3.2 (2013): 185-200.
Yeh, Hsin-Chih, et al. "A fluorescence light-up Ag nanocluster probe that discriminates single-nucleotide variants by emission color." *Journal of the American Chemical Society* 134.28 (2012): 11550.

* cited by examiner

*Primary Examiner* — Ethan C Whisenant
(74) *Attorney, Agent, or Firm* — Parker Highlander, PLLC

(57) ABSTRACT

In one embodiment, compositions and methods are provided for the detection and/or quantification of epigenetic modifications in DNA. In particular aspects, probes are provided comprising fluorescent metal nanocluster beacons, which can selectively detect nucleic acids including an epigenetic modification.

14 Claims, 15 Drawing Sheets
(3 of 15 Drawing Sheet(s) Filed in Color)
Specification includes a Sequence Listing.

METAL NANOCLUSTER BEACONS FOR DETECTION OF EPIGENTIC MODIFICATIONS

CROSS-REFERENCE TO RELATED APPLICATIONS

This application claims the benefit of U.S. Provisional Patent Application No. 62/202,424, filed Aug. 7, 2015, the entirety of which is incorporated herein by reference.

INCORPORATION OF SEQUENCE LISTING

The sequence listing that is contained in the file named "UTSBP1074US_ST25.txt", which is 8 KB (as measured in Microsoft Windows®) and was created on Aug. 5, 2016, is filed herewith by electronic submission and is incorporated by reference herein.

BACKGROUND OF THE INVENTION

1. Field of the Invention

The present invention relates generally to the field of molecular biology. More particularly, it concerns nucleic acid based probes and their uses for detecting epigenetic modifications in nucleic acid.

2. Description of Related Art

Epigenetic modifications are regarded as fundamental elements in gene expression regulation. DNA methylation, one such modification, plays crucial roles in widespread biological phenomena including host defense in bacteria and cell cycle regulation, gene imprinting, embryonic development and X-chromosome inactivation in mammals. Aberrant DNA methylation patterns in gene promoters are closely associated with perturbations in gene expression and have recently been indicated as a leading cause of human cancers. Likewise, $N^6$-methyladenosine, a ubiquitous modification in prokaryotic and eukaryotic genomes, is related to many biological functions and human diseases in different tissues and cancer cell lines with the highest levels detected in the brain, heart and kidney (Meyer at al., 2014). Epigenetic modifications, such as $N^6$-methyladenosine modification, are also involved in various physiological processes such as obesity, synaptic signaling, sperm development, stem cell differentiation, circadian periods, yeast meiosis, plant development and oogenesis. However, despite the importance of epigenetic modifications and rapid and significant advances in gene sequencing technology, methods for detecting and quantifying epigenetic changes remain elusive.

SUMMARY OF THE INVENTION

Embodiments of the present invention provide methods and compositions for the detection and quantification of epigenetic modifications in nucleic acid sequences. For example, in a first embodiment there is provided metal nanocluster beacon probes that can discriminate between unmodified and epigenetically modified nucleic acid sequences. In one aspect, a probe set is provided comprising: (a) a first probe comprising (i) a hybridization sequence that is complementary to a first sequence in a test nucleic acid sample; (ii) a recognition nucleotide that interacts with a candidate nucleotide in the test nucleic acid sample, said candidate nucleotide being a candidate for the epigenetic modification; and (iii) a nucleation sequence comprising a fluorescent metal nanocluster; and (b) a second probe comprising (iv) an enhancer sequence that enhances fluorescence of the fluorescent metal nanocluster when the enhancer sequence interacts with the nucleation sequence of the first probe; (v) an abasic site; and (vi) a hybridization sequence that is complementary to a second sequence in a test nucleic acid sample. Alternatively, a probe set of the embodiments may comprise: (a) a first probe comprising (i) a hybridization sequence that is complementary to a first sequence in a test nucleic acid sample; (ii) an abasic site; and (iii) a nucleation sequence comprising a fluorescent metal nanocluster; and (b) a second probe comprising (iv) an enhancer sequence that enhances fluorescence of the fluorescent metal nanocluster when the enhancer sequence interacts with the nucleation sequence of the first probe; (v) a recognition nucleotide that interacts with a candidate nucleotide in the test nucleic acid sample, said candidate nucleotide being a candidate for the epigenetic modification; and (vi) a hybridization sequence that is complementary to a second sequence in a test nucleic acid sample.

In a further embodiment there is provided provide a method for detecting an epigenetic modification in a test nucleic acid sample comprising: (I) hybridizing the test nucleic acid sample to a first and second probe, wherein (a) the first probe comprises (i) a hybridization sequence that is complementary to a first sequence in the test nucleic acid sample; (ii) a recognition nucleotide that interacts with a candidate nucleotide in the test nucleic acid sample, said candidate nucleotide being a candidate for the epigenetic modification; and (iii) a nucleation sequence comprising a fluorescent metal nanocluster; and (b) the second probe comprises (iv) an enhancer sequence that enhances fluorescence of the fluorescent metal nanocluster when the enhancer sequence interacts with the nucleation sequence of the first probe; (v) an abasic site; and (vi) a hybridization sequence that is complementary to a second sequence in the test nucleic acid sample; (II) exposing the test nucleic acid sample and the first and second probes to an excitation light; and (III) detecting a fluorescence signal from the fluorescent metal nanocluster, thereby detecting an epigenetic modification in the test nucleic acid sample. In certain aspects, the recognition nucleotide is a guanine, cytosine, adenine, thymine or uracil. In specific aspects, the recognition nucleotide is a guanine or a thymine.

In still a further embodiment a method for detecting an epigenetic modification in a test nucleic acid sample comprising: (I) hybridizing the test nucleic acid sample to a first and second probe, wherein (a) the first probe comprises (i) a hybridization sequence that is complementary to a first sequence in the test nucleic acid sample; (ii) an abasic site; and (iii) a nucleation sequence comprising a fluorescent metal nanocluster; and (b) the second probe comprises (iv) an enhancer sequence that enhances fluorescence of the fluorescent metal nanocluster when the enhancer sequence interacts with the nucleation sequence of the first probe; (v) a recognition nucleotide that interacts with a candidate nucleotide in the test nucleic acid sample, said candidate nucleotide being a candidate for the epigenetic modification; and (vi) a hybridization sequence that is complementary to a second sequence in the test nucleic acid sample; (II) exposing the test nucleic acid sample and the first and second probes to an excitation light; and (III) detecting a fluorescence signal from the fluorescent metal nanocluster, thereby detecting an epigenetic modification in the test nucleic acid sample. In certain aspects, the recognition nucleotide is a guanine, cytosine, adenine, thymine or uracil. In specific aspects, the recognition nucleotide is a guanine or a thymine.

In further aspects, the first sequence in a nucleic acid sample (such as a test or control sample) is positioned 5' relative to the second sequence of the nucleic acid sample. In certain aspects, the first sequence in a nucleic acid sample (such as a test or control sample) is positioned 3' relative to the second sequence of the nucleic acid sample. In particular aspects, the first sequence in the nucleic acid sample and the second sequence of the nucleic acid sample are separated by one nucleotide, which is the candidate nucleotide. Preferably, the first and/or second probe is at least 18, 19, 20, 21, 22, 23, 24, 25, 26, 27, 28, 29 or 30 nucleotides in length. In certain aspects, the first and/or second probe is a DNA or RNA probe. In further aspects, a first and/or second probe of the embodiments is a chimeric DNA/RNA probe.

In still further aspects, a first and second probe of the embodiments are comprised on single nucleic acid molecule. For example, a single nucleic acid molecule comprising a first and second probe may comprise, from 3' to 5' (i) a hybridization sequence that is complementary to a first sequence in the test nucleic acid sample; (ii) a recognition nucleotide that interacts with a candidate nucleotide in the test nucleic acid sample, said nucleotide being a candidate for the epigenetic modification; (iii) a nucleation sequence comprising a fluorescent metal nanocluster; (iv) a loop sequence; (v) an enhancer sequence that enhances fluorescence of the fluorescent metal nanocluster when the enhancer sequence interacts with the nucleation sequence of the first probe; (vi) an abasic site; and (vii) a hybridization sequence that is complementary to a second sequence in the test nucleic acid sample.

In further aspects, the step of detecting the fluorescence signal from the fluorescent metal nanocluster further comprises detecting a change in the fluorescence signal detected in the test nucleic acid sample as compared to a control nucleic acid sample. For example, the change in the fluorescence signal is a change in the wavelength of the fluorescence signal. In certain aspects, the change in the fluorescence signal is a change of at least 1, 2, 3, 4, 5, 6, 7, 8 9, or 10 nm in the wavelength of the fluorescence signal. Thus, in some aspects the fluorescent metal nanocluster fluoresces in a visible color upon excitation. In certain aspects, the excitation light is ultraviolet light, visible light, or near infrared light. For example, the excitation light comprises a wavelength of from 200 nm to 2000 nm. In certain aspects, the excitation light is provided by a laser.

In still further aspects, the step of detecting the fluorescence signal from the fluorescent metal nanocluster further comprises quantifying the fluorescence signal from the fluorescent metal nanocluster, thereby quantifying the proportion of nucleic acid molecules in the sample that comprise the epigenetic modification. For example, quantifying the fluorescence signal from the fluorescent metal nanocluster comprises quantifying a change in the fluorescence signal detected in the test nucleic acid sample as compared to a control nucleic acid sample.

In certain aspects, a control nucleic acid sample comprises nucleic acid molecules that are known to include or not include a given epigenetic modification. In further aspects, the control nucleic acid sample comprises nucleic acid molecules a known proportion of which include the epigenetic modification.

In certain aspects, an epigenetic modification for detection according to the embodiments is selected from the group consisting of 5-methylcytosine, $N^4$-methylcytosine, 5-hydroxymethylcytosine, $N^7$-methylguanosine and $N^6$-methyladenine. In exemplary aspects, the epigenetic modification is $N^6$-methyladenine. In some aspects, the test and/or control nucleic acid sample is a DNA sample. In other aspects, the test and/or control nucleic acid sample is a RNA sample.

In certain specific aspects, a test nucleic acid sample comprises a GAT nucleic acid sequence wherein the A position in the GAT sequence is the candidate site for the epigenetic modification (e.g., a candidate $N^6$-methyladenine position). In further aspects, the test nucleic acid sample comprises a GATC nucleic acid sequence wherein the A position in the GATC sequence is the candidate site for the epigenetic modification. In these aspects, the recognition nucleotide for the probe is preferably a guanine.

In further aspects, the test nucleic acid sample comprises a CAG nucleic acid sequence, wherein the A position in the CAG sequence is the candidate site for the epigenetic modification (e.g., a candidate $N^6$-methyladenine position). In even further aspects, the test nucleic acid sample comprises a CTGCAG nucleic acid sequence, wherein the A position in the CTGCAG sequence is the candidate site for the epigenetic modification. In these aspects, the recognition nucleotide for the probe is preferably a thymine.

In particular embodiments, the metal of the fluorescent metal nanocluster comprises silver, gold or copper. In exemplary methods, the metal of the fluorescent metal nanocluster comprises silver. Methods for the use of such fluorescent metal nanoclusters are provided, for instance, in U.S. Patent Publication No. 20140349289, which is incorporated herein by reference.

In some aspects, an enhancer sequence of the embodiments enhances fluorescence emission of the fluorescent metal nanocluster by at least 1.5, 2, 2.5, 3, 4 or 5-fold, when the enhancer sequence interacts with the nucleation sequence of the first probe (e.g., when the enhancer sequence is positioned in close proximity to the fluorescent metal nanocluster). In certain aspects, the enhancer sequence of the second probe comprises at least 30%, 35%, 40%, 45%, or 50% guanine positions. Preferably, the hybridization sequence of the first and/or second probe is at least 8, 9, 10, 11, 12, 13, 14, 15, 16, 17, 18, 19 or 20 nucleotides in length.

In another embodiment there is provided a composition comprising (a) a test nucleic acid comprising a first and a second sequence, wherein said first and second sequence are separated by one nucleotide, which comprises an epigenetic modification; (b) a first probe hybridized to the test nucleic acid, the first probe comprising (i) a hybridization sequence that is complementary to the first sequence in the test nucleic acid; (ii) a recognition nucleotide that interacts with the nucleotide that comprises the epigenetic modification in the test nucleic acid; and (iii) a nucleation sequence comprising a fluorescent metal nanocluster; and (c) a second probe hybridized to the test nucleic acid, the second probe comprising (iv) an enhancer sequence that enhances fluorescence of the fluorescent metal nanocluster when the enhancer sequence interacts with the nucleation sequence of the first probe; (v) an abasic site; and (vi) a hybridization sequence that is complementary to a second sequence in the test nucleic acid sample.

In a further embodiment there is provided a composition comprising (a) a test nucleic acid comprising a first and a second sequence, wherein said first and second sequence are separated by one nucleotide, which comprises an epigenetic modification; (b) a first probe hybridized to the test nucleic acid, the first probe comprising (i) a hybridization sequence that is complementary to the first sequence in the test nucleic acid; (ii) an abasic site; and (iii) a nucleation sequence comprising a fluorescent metal nanocluster; and (c) a second probe hybridized to the test nucleic acid, the second probe comprising (iv) an enhancer sequence that enhances fluorescence of the fluorescent metal nanocluster when the enhancer sequence interacts with the nucleation sequence of the first probe; (v) a recognition nucleotide that interacts with the nucleotide that comprises the epigenetic modification in the test nucleic acid; and (vi) a hybridization sequence that is complementary to a second sequence in the test nucleic acid sample.

Another embodiment concerns a kit comprising: (a) a control nucleic acid comprising a first and a second sequence, wherein said first and second sequence are separated by one nucleotide, which comprises an epigenetic modification; (b) a first probe hybridized to the test nucleic acid, the first probe comprising (i) a hybridization sequence that is complementary to the first sequence in the control nucleic acid; (ii) a recognition nucleotide that interacts with the nucleotide that comprises the epigenetic modification in the control nucleic acid; and (iii) a nucleation sequence comprising a fluorescent metal nanocluster; and (c) a second probe hybridized to the test nucleic acid, the second probe comprising (iv) an enhancer sequence that enhances fluorescence of the fluorescent metal nanocluster when the enhancer sequence interacts with the nucleation sequence of the first probe; (v) an abasic site; and (vi) a hybridization sequence that is complementary to a second sequence in the control nucleic acid sample.

A further embodiment concerns a kit comprising: (a) a control nucleic acid comprising a first and a second sequence, wherein said first and second sequence are separated by one nucleotide, which comprises an epigenetic modification; (b) a first probe hybridized to the test nucleic acid, the first probe comprising (i) a hybridization sequence that is complementary to the first sequence in the control nucleic acid; (ii) an abasic site; and (iii) a nucleation sequence comprising a fluorescent metal nanocluster; and (c) a second probe hybridized to the test nucleic acid, the second probe comprising (iv) an enhancer sequence that enhances fluorescence of the fluorescent metal nanocluster when the enhancer sequence interacts with the nucleation sequence of the first probe; (v) a recognition nucleotide that interacts with the nucleotide that comprises the epigenetic modification in the control nucleic acid; and (vi) a hybridization sequence that is complementary to a second sequence in the control nucleic acid sample.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

DESCRIPTION OF ILLUSTRATIVE EMBODIMENTS

Figure 1:
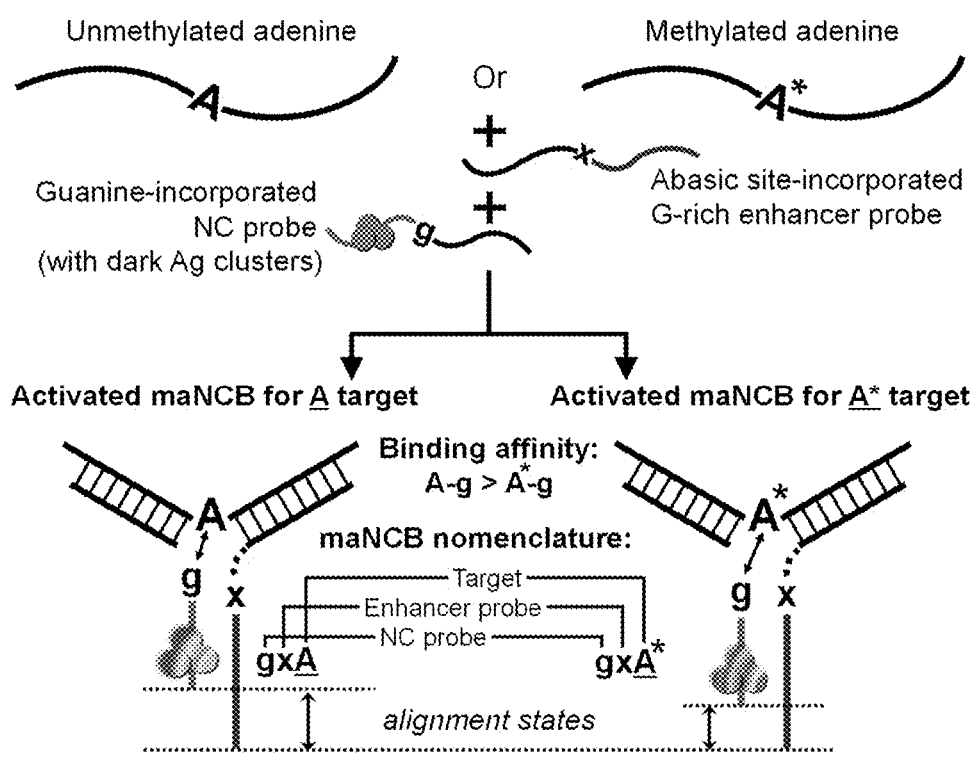
FIG. 1: $N^6$-methyladenine detection using methyladenine-specific NanoCluster Beacons (maNCBs) (not drawn to scale). Consisting of an NC probe (i.e. the cytosine-rich Ag cluster-nucleation sequence) and an enhancer probe (i.e. the guanine-rich sequence), maNCB forms two 3-way junctions (3WJ) when hybridizing with the two targets (A target or A* target; A* represents m6A). Here only the nucleotides-of-interest (A* or A) on the two targets and the recognition nucleotides on the two probes (n or x) are shown. The nomenclatures that represent the two resulting probe-target hybridization complexes are nxA and nxA*, respectively. The lowercase letters, n and x, indicate the recognition nucleotides on the NC and the enhancer probes, respectively. The capital letter represents the type of adenine on the target. Here x, the abasic site, serves as a non-interacting, neutral site, while the silver cluster-enhancer alignment is only controlled by the interactions between the NC probe's recognition nucleotide n and the nucleotides-of-interest on the targets. The maNCB design goal is thus to identify a suitable recognition nucleotide for the NC probe that can generate two differentiable silver cluster emission spectra upon probe-target binding.

Embodiments of the present invention provide compositions and methods for detecting and/or quantifying epigenetically modified nucleic acid molecules. In particular, it has been found that by using a paired probe set including a metal nanocluster and a probe having an enhancer sequence, epigenetically modified nucleotide positions can be detected in the same reaction by a change in fluorescence signal from the metal nanocluster. In some aspects, probes for use according to the embodiments comprise two single-stranded nucleic acid probes that are designed to complement with contiguous sections of a target nucleic acid. One of the probes of the pair includes a recognition nucleotide (which interacts with a candidate site for epigenetic modification on a target sequence) and a "nucleation portion" having a nucleotide sequence that can bind to metal nanoclusters. The other probe of the pair includes an "enhancer portion" that includes a nucleotide sequence which can produces an enhancement in fluorescence from the nanoclusters when the enhancer sequence is in sufficient proximity to the nanoclusters and the hybridized probe is subjected to excitation light (e.g., ultraviolet light). When the two probes are brought into sufficient proximity, such as by, binding the contiguous sections of the target nucleic acid sequence, the nucleation portion (and the metal nanoclusters) and the enhancement portion are in close proximity, which can be detected by detecting an increase in fluorescence intensity of the metal nanoclusters. However, when the target nucleic acid includes an epigenetic modification that interacts with the recognition nucleotide of the probe (e.g., a $N^6$-methyladenine) the alignment of the metal nanoclusters and the enhancer sequence is offset. Offsetting this alignment causes a resulting change in the wavelength (e.g., the fluorescence spectra) of the fluorescence emitted from the nanoclusters, which can be detected, and used to identify the variant in the variant target nucleic acid sequence. Moreover, the fluorescence intensity can be used to quantify the proportion of target nucleic acid molecules that include the given epigenetic modification.

I. DEFINITIONS

The term "complementary binding" as used herein occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'. Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

"Control" refers to a sample or standard used for comparison with an experimental sample. In some embodiments, the control is a sample obtained from a healthy subject (or a plurality of healthy subjects), such as a subject or subjects not expected or known to have a particular polymorphism. In additional embodiments, the control is a historical control or standard reference value or range of values (such as a previously tested control sample or plurality of such samples), or group of samples that represent baseline or normal values. A positive control can be an established standard that is indicative of a specific methylated nucleotide. In some embodiments a control nucleic acid is one that lacks a particular methylated nucleotide, and is used in assays for comparison with a test nucleic acid, to determine if the test nucleic acid includes the methylated nucleotide.

"Detecting" is used herein to identify the existence, presence, or fact of something. General methods of detecting are known to the skilled artisan and may be supplemented with the protocols and reagents disclosed herein. For example, included herein are methods of detecting a nucleic acid molecule in sample. Detection can include a physical readout, such as fluorescence output.

"Enhancer Sequence" refers to a nucleotide sequence that when placed in proximity to another nucleic acid molecule having templated metal nanoclusters increases the fluorescence intensity of the metal nanocluster when exposed to excitation light. Exemplary enhancer sequences are known in the art and disclosed herein.

"Excitation Light" refers to light of any wavelength that is capable of causing template metal nanoclusters to fluoresce. Non-limiting examples of excitation light include visible light, ultraviolet and near infrared light.

The term "hybridization" is defined as forming base pairs between complementary regions of two strands of DNA, RNA, or between DNA and RNA, thereby forming a duplex molecule, for example. Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11).

An "isolated" biological component (such as a nucleic acid molecule) has been substantially separated, produced apart from, or purified away from other biological components. Nucleic acid molecules which have been "isolated" include nucleic acids molecules purified by standard purification methods, as well as those chemically synthesized. Isolated does not require absolute purity, and can include nucleic acid molecules that are at least 50% isolated, such as at least 75%, 80%, 90%, 95%, 98%, 99% or even 100% isolated.

"Metal nanoclusters" are collections of small numbers (e.g., 2-30 atoms) of noble metal atoms (e.g., gold or silver atoms) with physical sizes close to the Fermi wavelength of an electron (~0.5 nm for gold and silver). The metal atoms can have affinity for nitrogen atoms on DNA, including the N3 of cytosine and the N7 of guanine. Metal nanoclusters for use with the disclosed embodiments are fluorescent, that is, they have the ability to emit light of a particular wavelength (emission wavelength) when exposed to light of another wavelength (excitation wavelength).

A "nucleation sequence" is a sequence of nucleotides capable of binding or associating with metal atoms to form template metal nanoclusters. The portion of a nucleic acid molecule including a nucleation sequence of nucleotides is referred to as the "nucleation portion" of the nucleic acid molecule. Exemplary nucleation sequences are known and provided herein. Specific nucleation sequences that are useful for interacting with metal nanoclusters and forming DNA templated metal nanoclusters are disclosed herein. Examples of metal nanoclusters for use as fluorescent reporters, and methods of producing templated metal nanoclusters on DNA oligonucleotides are known. See, e.g., U.S. Patent Publication No. US20110212540, incorporated by reference herein in its entirety, and U.S. Publication No. US20140349289, incorporated herein by reference.

A "nucleic acid" is a deoxyribonucleotide or ribonucleotide polymer, which can include analogues of natural nucleotides that hybridize to nucleic acid molecules in a manner similar to naturally occurring nucleotides. In a particular example, a nucleic acid molecule is a single stranded (ss) DNA or RNA molecule, such as a probe or primer. In another particular example, a nucleic acid molecule is a double stranded (ds) nucleic acid, such as a target nucleic acid. Examples of modified nucleic acids are those with altered backbones, such as peptide nucleic acids (PNA).

"Probes" are short nucleic acid molecules, usually DNA oligonucleotides, typically of about 20-100 nucleotides in length, used to detect the presence of a complementary target DNA strand in a sample. All or a portion of a probe can be annealed to a complementary target DNA strand by nucleic acid hybridization to form a hybrid between the primer and the target DNA strand. Therefore, probes can be used to identify a target nucleic acid molecule, wherein the sequence of the probe is specific for the target nucleic acid molecule, for example so that the probe will hybridize to the target nucleic acid molecule under very high stringency hybridization conditions.

Typically, probes include at least about 10 contiguous nucleotides, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 contiguous nucleotides, that are complementary to a target nucleic acid molecule, such as 20-70 nucleotides, 20-60 nucleotides, 20-50 nucleotides, 20-40 nucleotides, or 20-30 nucleotides. Probes can also be of a maximum length, for example no more than 20, 25, 25, 40, 50, 75 or 100 nucleotides in length. The specificity of a particular probe typically increases with an increase in the number of complementary nucleotides on the probe.

The probe can also include additional nucleotides that are not complementary to the target nucleic acid molecule. The additional nucleotides can be used, for example, for detection of the probe in a sample. In several embodiments, the probes disclosed herein include a hybridization portion that is complementary to a test nucleic acid sequence, and a nucleation portion (that can associate with metal nanoclusters) or an enhancer portion (that can enhance the fluorescence of metal nanoclusters associated with the nucleation portion. The additional nucleotides can be located 5' or 3' of the hybridization nucleotides.

Methods for preparing and using nucleic acid probes are described, for example, in Sambrook et al. (In Molecular Cloning: A Laboratory Manual, CSHL, New York, 1989), Ausubel et al. (ed.) (In Current Protocols in Molecular Biology, John Wiley & Sons, New York, 1998), and Innis et al. (PCR Protocols, A Guide to Methods and Applications, Academic Press, Inc., San Diego, Calif., 1990).

A "sample," such as a biological sample, is a sample obtained from a subject. As used herein, biological samples include all clinical samples useful for detection of a methylated nucleotide, including, but not limited to, cells, tissues, and bodily fluids, such as: blood; derivatives and fractions of blood, such as serum; urine; sputum; or CVS samples. In a particular example, a sample includes blood obtained from a human subject, such as whole blood or serum.

A "test nucleic acid molecule" refers to a nucleic acid molecule whose detection, quantitation, qualitative detection, characterization, or a combination thereof, is intended. For example, the test nucleic acid molecule can be a defined region or particular portion of a nucleic acid molecule, for example a portion of a genome (such as a gene or a region of DNA or RNA containing a gene (or portion thereof) of interest). The nucleic acid molecule need not be in a purified form. Various other nucleic acid molecules can also be present with the test nucleic acid molecule. For example, the test nucleic acid molecule can be a specific nucleic acid molecule (which can include RNA or DNA), for which the detection of a particular polymorphism is intended. In some examples, a test nucleic acid includes a viral nucleic acid molecule, or a bacterial nucleic acid molecule. Purification or isolation of the test nucleic acid molecule, if needed, can be conducted by methods known to those in the art, such as by using a commercially available purification kit or the like.

An "abasic" site or "AP (apurinic/apyrimidinic)" site is referred to herein as a location in nucleic acid (e.g., DNA or RNA) that has neither a purine nor a pyrimidine base. An abasic site may occur spontaneously or due to DNA damage. AP sites are one of the most frequent spontaneous lesions in DNA.

II. EPIGENETIC MODIFICATIONS

The number of nucleic acid modifications identified in the genomes and transcriptomes has exploded since the first discovery of non-canonical nucleobases six decades ago (Rozenski et al., 1999; McCloskey et al., 2005; Behm-Ansmant et al., 2011). Many of the modifications in genomes are heritable epigenetic marks that influence the way the genes are expressed and eventually define cell status among the higher organisms (Song et al., 2012). In particular, $N^6$-methyladenine (m6a) is a methylation modification abundant in prokaryotic genomes (Low et al., 2011), and also found in lower eukaryotes (Hattman 2005; Ratel et al., 2006; Wion et al., 2006) and higher plants (Vanyushin et al., 1988). While the biological functions of m6A at GATC sites in single-celled organisms are well studied (such as genome defense, mismatch repair and gene expression control (Marinus et al., 1987)), its roles in eukaryotic genomes remain largely unknown (Ratel et al., 2006).

So far detection of $N^6$-methyladenine in DNA has been demonstrated using a single-molecule, real-time sequencing method (Flusberg et al., 2010). Detection of $N^6$-methyladenosine in RNA has been shown using (1) nuclease cleavage followed by thin-layer chromatography (TLC) or mass spectrometry (MS) (Kellner et al., 2010), (2) immunocapturing of m6A-containing RNA fragments followed by sequencing (Dominissini et al., 2013), (3) ligation (Dai et al., 2007), and (4) a selective polymerase (Harcourt et al., 2013). However, these methods are laborious (e.g. require multiple steps to identify a single site), time-consuming (e.g. TLC and MS), and high-cost (e.g. enzymatic reaction). Whereas high-resolution melting (HRM) analysis is able to detect a single m6A modification within a target DNA via the destabilizing effect of m6A, HRM cannot pinpoint the location of m6A in the sequence (Lopez et al., 2012). A simple and cost-effective way to identify single m6A at any specific sites is therefore highly desired.

The techniques detailed here provide robust, simple, enzyme-free and hybridization-based method for m6A detection with pinpoint specificity, using a new type of silver cluster-based DNA probe which are termed methyladenine-specific NanoCluster Beacon (maNCB). Yeh and co-workers have previously introduced a NanoCluster Beacon (NCB) that fluoresces upon binding to a DNA target (Yeh et al., 2010; Yeh et al., 2011; Obliosca et al., 2014; Juul et al., 2015). NCBs employ DNA-templated, few-atom silver nanoclusters (DNA/Ag NCs, about 2-20 silver atoms per cluster) as reporters whose fluorescence can be significantly enhanced through interactions with a nearby G-rich sequence (called an enhancer). Not only is the fluorescence of silver clusters activated, but the fluorescence color can also respond to the "alignment" of silver cluster with respect to the enhancer sequence (Yeh et al., 2012). In other words, the fluorescence emission of silver clusters is sensitive to the nucleobase environment surrounding the clusters. Taking advantage of this fluorescence tunability by altering the surrounding ligands, a property that is not commonly seen among existing reporters (Oblisosca et al., 2013), NCB soon evolved to a multicolor probe, termed chameleon NanoCluster Beacon (cNCB), for single-nucleotide polymorphism (SNP) detection (Yeh et al., 2012). Here we bring the NCB detection to the next level by designing a new NCB specifically for m6A detection.

III. DETECTING METHYLATED NUCLEOTIDES

A method is disclosed for detecting a methylated nucleotide between a test nucleic acid and a control nucleic acid using metal nanocluster beacons (NCB). The NCB includes two probes that each include portions complementary to contiguous sections of the control nucleic acid sequence. The two probes can also include regions of complementarity with each other, e.g., to make the three-way-junction (3WJ) discussed below. One of the probes of the NCB includes a "nucleation portion" that includes a nucleotide sequence that can bind to metal nanoclusters. The other probe of the NCB includes an "enhancer portion" that includes a nucleotide sequence that can enhance fluorescence emitted from the nanoclusters when in sufficient proximity to the nanoclusters. When the two probes are brought into sufficient proximity by binding the contiguous sections of the control nucleic acid sequence, the nucleation portion (and the metal nanoclusters) and the enhancement portion are in close proximity, which can be detected by detecting an increase in fluorescence intensity of the metal nanoclusters.

The first probe also includes a nucleation portion including templated metal nanoclusters, which can fluoresce when exposed to excitation light (e.g., UV light). The second probe includes an enhancer portion including a nucleotide sequence that enhances fluorescent emission from the metal nanoclusters when associated with the metal nanoclusters.

The test mixture is exposed to excitation light, and any corresponding fluorescence is measured. Detecting a difference in the wavelength of the fluorescence emission of the test mixture compared to that of a corresponding control mixture comprising the first probe, the second probe, and the control nucleic acid molecule detects the presence of a methylated nucleotide in the test nucleic acid molecule compared to the control nucleic acid molecule. The difference in wavelength fluorescence emission between the test mixture and the control mixture can be a visible color difference. In more embodiments, the difference in wavelength fluorescence emission between the test mixture and the control mixture is at least 1 nm (such as at least 2, 3, 4, 5, 6, 7, 8, 9, 10, 15, 20, 25, 30, 40, 50, 60, 70, 80, 90, or 100 nm). The test nucleic acid molecule may be compared to multiple different reference standard nucleic acid molecules.

In some embodiments, the methylated nucleotide is $N^6$-methyladenine. For example, the probes hydridize around methylated or unmethylated adenosine. The measured fluorescence of the control mixture serves as a reference standard for comparison purposes to the measured fluorescence of the test mixture. Where the control mixture and the test mixture provide the same or substantially similar measurable wavelength or range of wavelengths upon exposure to excitation light, it may be concluded that the test nucleic acid molecule and the control nucleic acid molecule have the same nucleotide sequence across the junction of the hybridization portions of the first and second probes. Where the control mixture and the test mixture provide the different measurable wavelength or range of wavelengths upon exposure to excitation light, it may be concluded that the test nucleic acid molecule and the control nucleic acid molecule do not have the same nucleotide sequence across the junction of the hybridization portions of the first and second probes. In certain aspects, the measured fluorescence between the control mixture and test mixture provides quantification of the $N^6$-methyladenine.

A. Metal Nanoclusters

The disclosed embodiments take advantage of the fluorescent properties of metal (e.g., silver) nanoclusters when the nanoclusters are brought near a DNA sequence referred to herein as an "enhancer sequence". The metal of the templated metal nanoclusters can be a noble metal, such as silver, gold, or copper. DNA-templated silver nanoclusters can emit colored light through interactions with "enhancer" sequences. The color of the emitted light was found to depend on the particular enhancer sequence. Silver nanoclusters are groups of from about 2 to about 30 silver atoms that are sub 2 nm in size with the properties of good fluorescence, good photostability, and electroluminescence. These silver nanoclusters, which are templated on the nucleation sequence of an embodiment probe, function as fluorescence reporters.

To form metal nanoclusters on DNA, positively charged metal ions (e.g., Ag+ atoms) are first attached to ssDNA (e.g., cytosine nucleotides) spontaneously in solution. Then, a reductant (e.g., sodium borohydride) is added to reduce the charge of the atoms (e.g., Ag+ to Ag(0)), after which metal atom "clusters" will form. The ssDNA prevents the metal cluster "from growing out of control". Clusters that become a "nanoparticle" (size >5 nm) are not fluorescent.

Examples of metal nanoclusters for use as fluorescent reporters, and methods of producing templated metal nanoclusters on DNA oligonucleotides are known. See U.S. Pat. App. Pub. 2011/0212540, incorporated by reference herein in its entirety. The basis for the operation of the templated metal nanoclusters is a controlled conversion of DNA-templated silver nanoclusters between a dark, non-emissive state, which is their state when not associated with an enhancer sequence, and a bright, emissive state when associated with the enhancer sequence. Unlike prior use of metal nanoclusters, the present method involves tuning the fluorescent emission properties of the metal nanoclusters (e.g., a wavelength shift of 60-70 nm) by altering the relative positions of Noble metal nanoclusters, such as those made of silver, gold, copper, or other noble metals typically include collections of a number of metal atoms (approximately 2-30 atoms or 2, 3, 4, 5, 6, 7, 8, 9, 10, 11, 12, 13, 14, 15, 16, 17, 18, 19, 20, 21, 22, 23, 24, 25, 26, 27, 28, 29 or 30 atoms) with physical sizes close to the Fermi wavelength of an electron (e.g., about 0.5 nm for gold and silver). They behave like molecular systems and yield fluorescence emission in the UV-visible and infrared range. In some examples, oligonucleotide-templated silver nanoclusters ("DNA/Ag NCs"), which are a versatile set of fluorophores that have been used for a variety of applications including live cell imaging, detection of specific metal ions, and single-nucleotide variation identification. DNA/Ag NCs can be biocompatible and can have better photostability than commonly used organic dyes. Unlike organic dyes and photoluminescent nanocrystals, they are subject to silver oxidation/reduction or nanocluster ("NC") regrouping, which results in conversion among different NC species. These different species may provide different color emissions.

In the disclosed embodiments, the proximity of metal nanoclusters with an enhancer sequence occurs when the NC and enhancer portions of two probes of the NCB are brought into close proximity by the hybridization of the hybridization portion of the probes with a contiguous portion of a target nucleic acid molecule. Prior to hybridization, the nanoclusters are only weakly fluorescent or non-fluorescent. After hybridization, the fluorescence emission from the silver nanoclusters is enhanced (the probe "lights up") because the nanoclusters which are templated onto the nucleation sequence are brought into proximity with the guanine(s) from the enhancer sequence. As discussed in more detail herein, by altering the alignment of the metal nanoclusters with the enhancer sequence, the emission wavelength of light emitted from the nanoclusters can be altered.

The association of the metal nanoclusters on the first probe with the enhancement portion of the second probe can increase the fluorescence emission of the templated metal nanoclusters by at least 2-fold fold. In a related aspect, the association of the metal nanoclusters on the first probe with the enhancement portion of the second probe can increase the fluorescence emission of the templated metal nanoclusters from about 2-fold to about 500-fold (such as about 2, 3, 4, 5, 6, 7, 8, 9, 10, 20, 30, 40, 50, 60, 70, 80, 90, 100, 125, 150, 175, 200, 225, 250, 275, 300, 325, 350, 375, 400, 425, 450, 475 or 500-fold).

Detection of fluorescence emission can be performed according to known methods, for example as described herein. The excitation light can be selected from the group consisting of ultraviolet light, visible light, near infrared light or a combination thereof. In a related aspect, the wavelength of excitation light is from 200 nm to 2000 nm (or 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1050, 1100, 1150, 1200, 1250, 1300, 1350, 1400, 1450, 1500, 1550, 1600, 1650, 1700, 1750, 1800, 1850, 1900, 1950 or 2000 nm).

B. Nucleic Acid Samples

DNA and/or RNA samples may be obtained from a variety of sources, as further detailed herein. In certain cases, a plurality of nucleic acid samples are analyzed in parallel. Samples for parallel analysis may include a nucleic acid standard having a known level of methylation. Likewise, a plurality of different oligonucleotide probes may be employed to determine methylation status at multiple regions within a nucleic acid sample.

Exemplary eukaryotic nucleic acids that can be used in a method of the invention includes, without limitation, mammal nucleic acids such as a rodent, mouse, rat, rabbit, guinea pig, ungulate, horse, sheep, pig, goat, cow, cat, dog, primate, human or non-human primate. Plant DNA may also be analyzed according to the invention. For example, nucleic acids from *Arabidopsis thaliana*, maize, sorghum, oat, wheat, rice, canola, or soybean may be analyzed. It is further contemplated that nucleic acid from other organisms such as algae, a nematodes, insects (e.g., *Drosophila melanogaster*, mosquito, fruit fly, honey bee or spider), fish, reptiles, amphibians and yeast may be analyzed.

As indicated above, DNA and/or RNA can be isolated from one or more cells, bodily fluids or tissues. An array of methods can be used to isolate DNA and/or RNA from samples such as blood, sweat, tears, lymph, urine, saliva, semen, cerebrospinal fluid, feces or amniotic fluid. Genomic DNA can also be obtained from one or more cell or tissue in primary culture, in a propagated cell line, a fixed archival sample, forensic sample or archeological sample. Methods for isolating genomic DNA and/or RNA from a cell, fluid or tissue are well known in the art (see, e.g., Sambrook et al., 2001).

Exemplary cell types from which nucleic acids can be obtained in a method of the invention include, a blood cell such as a B lymphocyte, T lymphocyte, leukocyte, erythrocyte, macrophage, or neutrophil; a muscle cell such as a skeletal cell, smooth muscle cell or cardiac muscle cell; germ cell such as a sperm or egg; epithelial cell; connective tissue cell such as an adipocyte, fibroblast or osteoblast; neuron; astrocyte; stromal cell; kidney cell; pancreatic cell; liver cell; or keratinocyte. A cell from which DNA and/or RNA is obtained can be at a particular developmental level including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Other cells include a bone marrow stromal cell (mesenchymal stem cell) or a cell that develops therefrom such as a bone cell (osteocyte), cartilage cells (chondrocyte), fat cell (adipocyte), or other kinds of connective tissue cells such as one found in tendons; neural stem cell or a cell it gives rise to including, for example, a nerve cells (neuron), astrocyte or oligodendrocyte; epithelial stem cell or a cell that arises from an epithelial stem cell such as an absorptive cell, goblet cell, Paneth cell, or enteroendocrine cell; skin stem cell; epidermal stem cell; or follicular stem cell. Generally any type of stem cell can be used including, without limitation, an embryonic stem cell, adult stem cell, totipotent stem cell or pluripotent stem cell.

A cell from which a nucleic acid sample is obtained for use in the invention can be a normal cell or a cell displaying one or more symptom of a particular disease or condition. Thus, a nucleic acid sample used in a method of the invention can be obtained from a cancer cell, neoplastic cell, apoptotic cell, senescent cell, necrotic cell, an autoimmune cell, a call comprising a heritable genetic disease or the like.

Additionally, the test and control nucleic acids can be processed or manipulated, such as being amplified, digested by restriction endonucleases, or labeled. In some embodiments, the nucleic acids are diluted in one or more solutions, arranged in an array, and/or placed on a solid substrate (for example, a DNA microchip). In certain embodiments, the nucleic acids are diluted in an organic or inorganic solvent to form solutions. The solution optionally can contain additives, such as stabilizers, preservatives, or buffers.

The target DNA samples may contain specific sequences for hybridization to the probes. For example, for detection of m6A, targets may be GATC and/or CTGCAG-containing target samples.

IV. REAGENTS AND KITS

The kits may comprise suitably aliquoted reagents of the present invention, such as an enhancer probe and NC probe. Additional components that may be included in a kit according to the invention include, but are not limited to, control oligonucleotides (e.g., methylated and non-methylated oligonucleotides), distilled water, probes, dyes, sample vials and instructions for performing methylation quantification assays. In certain further aspects, reagents for DNA isolation, DNA purification and/or DNA clean-up may also be included in a kit. In some examples, one or more sets of probes, may be provided in pre-measured single use amounts in individual, typically disposable, tubes or equivalent containers. With such an arrangement, the sample to be tested for the presence of the target nucleic acids can be added to the individual tube(s) and amplification carried out directly. In some embodiments, kits also may include the reagents necessary to carry out fluorescence detection assays, including sample preparation reagents, appropriate buffers, salts, tubes or assay cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing reagent containers in close confinement for commercial sale. Such containers may include cardboard containers or injection or blow-molded plastic containers into which the desired vials are retained.

When the components of the kit are provided in one or more liquid solutions, the liquid solution is an aqueous solution, with a sterile aqueous solution being preferred. However, the components of the kit may be provided as dried powder(s). When reagents and/or components are provided as a dry powder, the powder can be reconstituted by the addition of a suitable solvent. It is envisioned that the solvent may also be provided in another container means.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Methyladenine-Specific NanoCluster Beacons for GATC-Containing Targets Similar to cNCB, maNCB adopts a binary probe configuration that forms a 3-way junction (3WJ) with the DNA target (FIG. 1). Consisting of an NC probe (i.e. the C-rich Ag cluster-nucleation sequence shown in blue) and an enhancer probe (i.e. the G-rich sequence shown in red), maNCB binds to the target around the "nucleotide-of-interest," which is either m6A (N6-methyladenine, denoted as A* in FIG. 1) or A (unmethylated adenine) in this study. Since the most common occurrence of m6A was identified within GATC sites (Marinus et al., 2009), two 60-nt long targets containing either a GATC or a GA*TC site were synthesized (Target Set 1 in Table 1). These two targets have exactly identical sequences except for a single-nucleotide substitution (A→A*) in the middle (denoted as the "A target" and the "A* target" respectively in FIG. 1). Upon 3WJ formation between the probe and the target, two "recognition nucleotides" (one on the NC probe and the other on the enhancer probe) are brought close to the nucleotide-of-interest on the target. In the previous SNP detection using cNCB, Watson-Crick basepairing is formed between the nucleotide-of-interest and one of the recognition nucleotides, leading to two distinct alignment states between the silver cluster and the enhancer sequence. The main task in the maNCB design is therefore to search for a set of recognition nucleotides that can discriminate m6A from A by distinct emission spectra of activated silver clusters.

TABLE 1

Oligonucleotide sequences of maNCBs used for Target Sets 1 and 2.

| Name | DNA Sequence (5'→3') |
|---|---|
| Target Set 1 | |
| Unmethylated target (SEQ ID NO. 1) | ATC AAG TAC AGA TCA TGC GTT GCA CGG TCG ATC AAG TAC AGA TCA TGC GTC GGG CTC GGA |
| Methylated target (SEQ ID NO. 2) | ATC AAG TAC AGA TCA TGC GTT GCA CGG TCG A*TC AAG TAC AGA TCA TGC GTC GGG CTC GGA |
| maNCB_1 | |
| NC probe (SEQ ID NO. 3) | CCC TTA ATC CCC g CGA CCG TGC AAC GCA TGA TCT GTA |
| Enhancer probe (SEQ ID NO. 4) | CCC GAC GCA TGA TCT GTA CTT GAx GGG TGG GGT GGG GTG GGG |
| Control NC Probes_1 | |
| NC Probe_a (SEQ ID NO. 5) | CCC TTA ATC CCC a CGA CCG TGC AAC GCA TGA TCT GTA |
| NC Probe_t (SEQ ID NO. 6) | CCC TTA ATC CCC t CGA CCG TGC AAC GCA TGA TCT GTA |
| maNCB_5 | |
| NC probe (SEQ ID NO. 7) | CCC TTA ATC CCC g ACT TGA TCG ACC GTG CAA CGC ATG |
| Enhancer probe (SEQ ID NO. 8) | TCC GAG CCC GAC GCA TGA TCT GxG GGT GGG GTG GGG TGG GG |
| Target Set 2 | |
| Unmethylated target (SEQ ID NO. 9) | CTA GTT TAA TTT TGT TTT GTG GGT TAA AAG ATC GTT TAA ATC AAT ATT TAC AAC ATA AAA |
| Methylated target (SEQ ID NO. 10) | CTA GTT TAA TTT TGT TTT GTG GGT TAA AAG A*TC GTT TAA ATC AAT ATT TAC AAC ATA AAA |

TABLE 1-continued

Oligonucleotide sequences of maNCBs used for Target Sets 1 and 2.

| Name | DNA Sequence (5'→3') |
|---|---|
| maNCB_2 | |
| NC probe (SEQ ID NO. 11) | CCC TTA ATC CCC g CTT TTA ACC CAC AAA ACA AAA TTA |
| Enhancer probe (SEQ ID NO. 12) | GTT GTA AAT ATT GAT TTA AAC GAx GGG TGG GGT GGG GTG GGG |
| Control NC Probes_2 | |
| NC Probe_a (SEQ ID NO. 13) | CCC TTA ATC CCC a CTT TTA ACC CAC AAA ACA AAA TTA |
| NC Probe_t (SEQ ID NO. 14) | CCC TTA ATC CCC t CTT TTA ACC CAC AAA ACA AAA TTA |

Included are the unmethylated adenine (A) and N6-methyladenine (denoted as A*), the cytosine-rich nucleation sequence, the recognition nucleotide, the hybridization sequence, the abasic site (x) and the G-rich enhancer sequence. Target 1 is a synthetic target (Flusberg et al., 2010) while Target 2 (Cooper et al., 2014) is related to a stx2A CDS gene (GenBank: CP006027.1; 3,056,718 . . . 3,056,777).

Figure 2A:
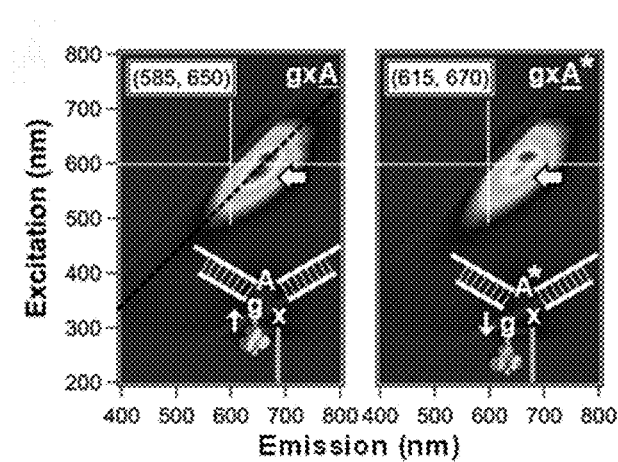
FIGS. 2A-2D: (A) 2D fluorescence contour plots of gxA and gxA* that clearly differentiate between A* and A targets (indicated by thick arrows). The only difference between these two targets (60-nt long) is an A to A* (m6A) substitution right in the middle of the sequence (Target Set 1 in Table 1). Arrow pointing upwards indicates a stronger A-g interaction as compared to A*-g interaction. (B) Emission profiles of gxA and gxA* (intensity normalized at 670 nm) along the dashed line in A (with Stokes shift of 60 nm). Error bars (represented by ribbons) show standard deviations from five trials. The P value is found to be 0.0001 at 645 nm. (C-D) When using t or a as recognition nucleotides (txA vs. txA* and axA vs. axA*), no significant changes in 2D spectra are observed. The target sequence used here has the GATC motif (Target Set 1).
Figure 2B:
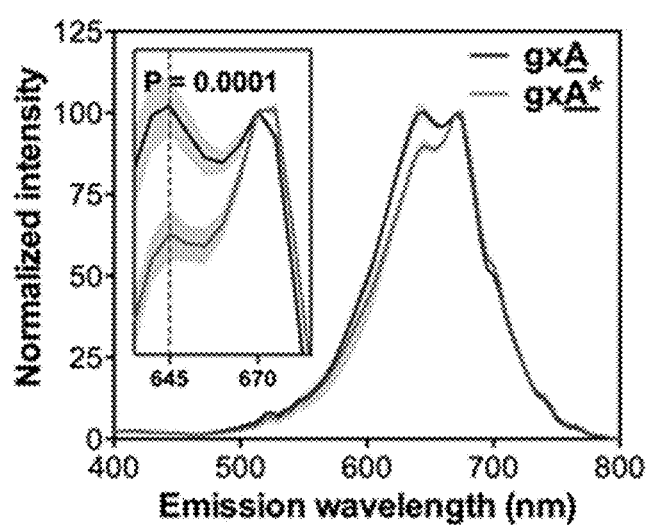
Figure 2C:
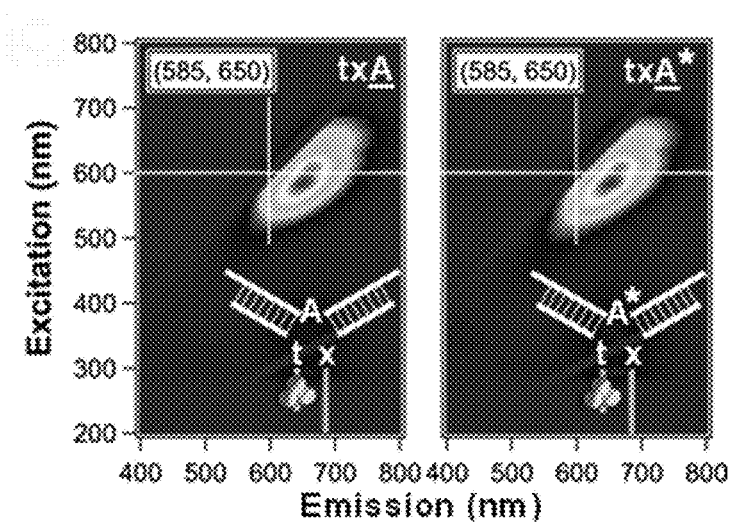
Figure 2D:
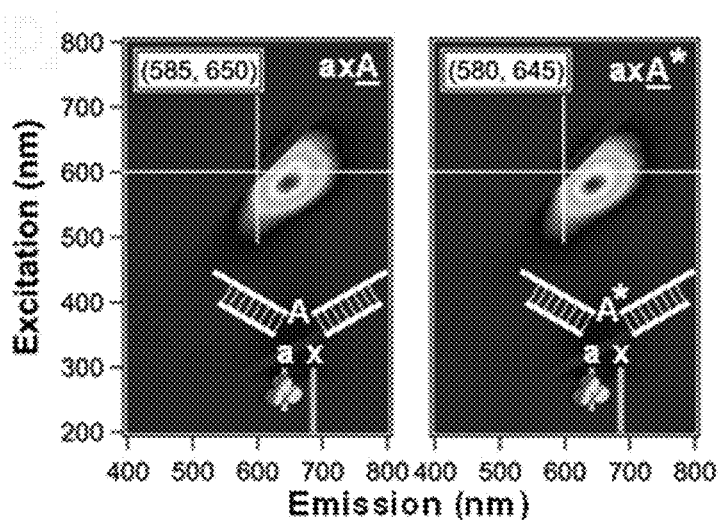
Figure 3A:
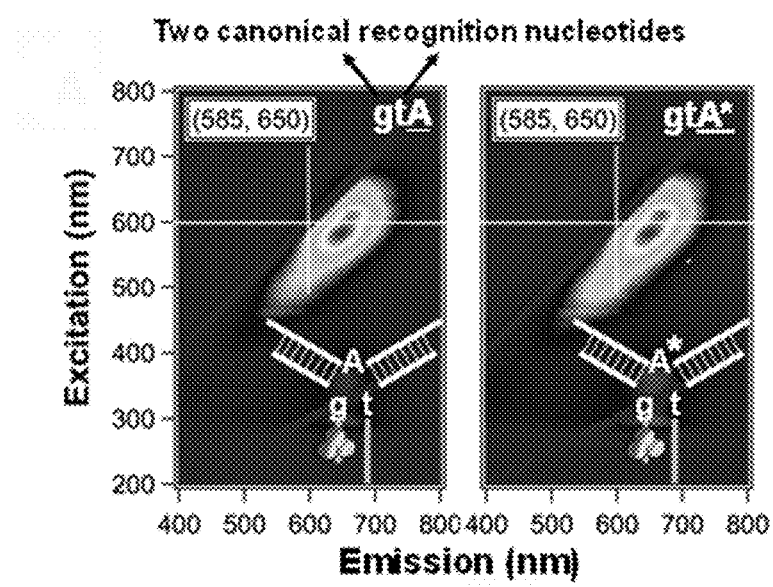
FIGS. 3A-3C: maNCBs containing two canonical recognition nucleotides failed to discriminate A* target from A target. 2D fluorescence contour plots of the selected recognition nucleotide combinations: (A) gtA vs. gtA*, (B) ttA vs. ttA* and (C) atA vs. atA*. None of these sets show significant changes in their emission spectra. Target sequence used here has the GATC motif (Target Set 1).
Figure 3B:
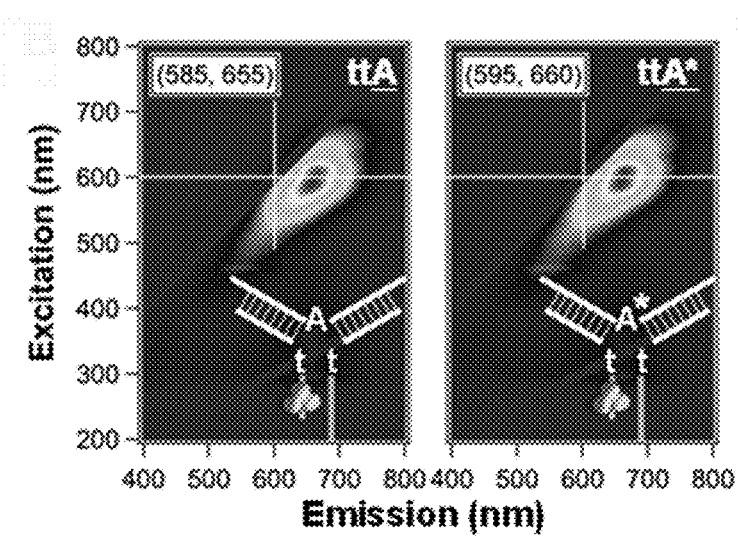
Figure 3C:
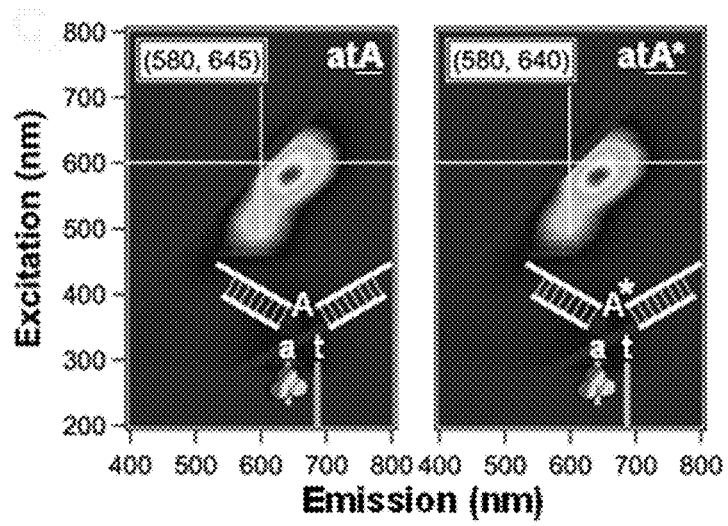
Figure 4A:
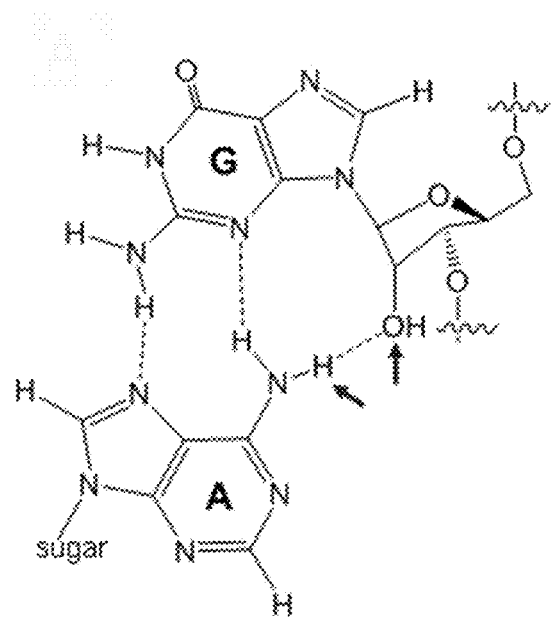
FIGS. 4A-4B: (A) A-G base pairing via trans Hoogsteen/sugar edge configuration is found in many RNA structures. In this purine-purine base pairing, $N^6H$ of A and 2'OH of G are in close proximity to each other (indicated by arrows), forming a hydrogen bond between them. (B) Presence of the bulky $N^6$-methyl group of $m^6A$ (denoted as A*) hinders the above H-bond formation and may sterically clash with the phosphate backbone of $G^9$ (indicated by arrows), causing A*-G base pair to be weaker than A-G pair.
Figure 4B:
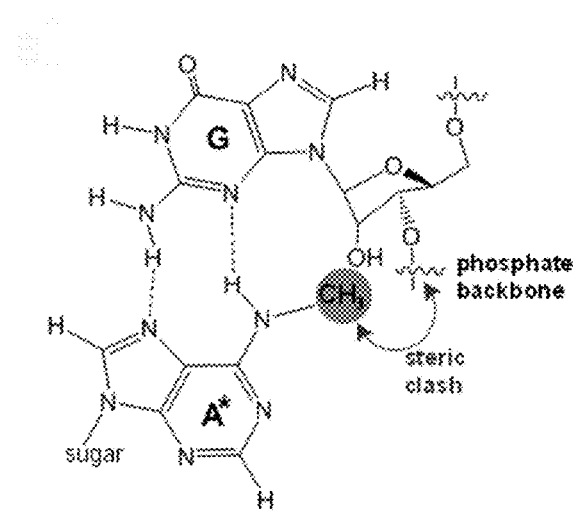
Figure 5:
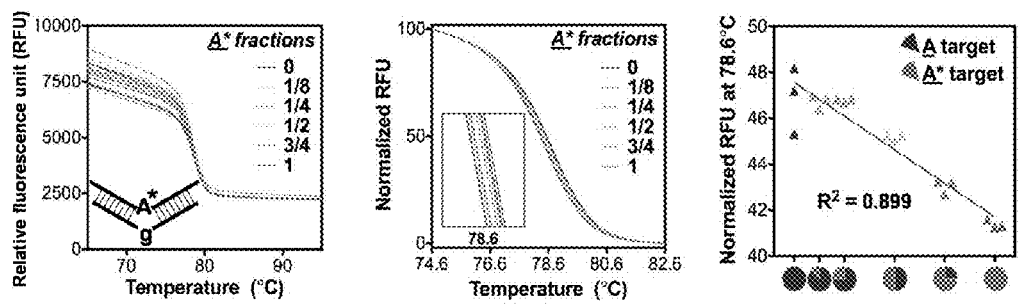
FIG. 5: Quantification of adenine methylation extent in heterogeneous samples using high-resolution melting analysis. High-resolution melting analysis were performed in the six dsDNA mixtures. Here fraction 0 means 100% A target and fraction 1 means 100% A* target. Fraction 0 has higher intensity while fraction 1 has lower intensity. After normalization at 75° C. and 83° C. ($T_m\pm4°$ C.), intercalating dye's emission intensity at 79° C. is found correlated to the amount of A* target in the mixture ($R^2$=0.899). Target sequence used here has the GATC motif (Target Set 1). The dsDNA used here contains either an A-g or an A*-g base pair in the sequence (different from the dsDNA used in FIG. 3B). The melting temperatures of fraction 0 and 1 samples indicate that the A-g pair is more stable than the A*-g pair even in DNA.

The inventors tested all recognition nucleotide combinations but failed to achieve a working maNCB design (FIG. 3). In the second attempt, the number of recognition nucleotides was reduced from two to one by introducing an AP site to the enhancer probe (denoted as x in FIG. 1). Out of the four recognition nucleotides tested on the NC probe, only g could give differentiable silver cluster emission spectra upon probe-target binding (spectrum difference pointed by arrows in FIG. 2A). The difference in 2D spectra can be more clearly seen in 1D spectra (FIG. 2B), which were plotted along a 45° line (with a fixed Stokes shift of 60 nm) and normalized at 670 nm. The two 1D spectra unambiguously deviated from each other at 645 nm, with p value of about 0.0001. On the other hand, when other recognition nucleotides were used, no differentiation was observed (FIGS. 2C and 2D). The discrimination given by g must be due to different interaction strengths between A-g and A*-g. Dai et al. have previously identified guanine to be the most effective recognition base in their ligation-based method for N6-methyladenosine detection on a RNA target (Dai et al., 2007). In RNA, adenosine can form a sheared, non-Watson-Crick base pair with guanosine, in which three hydrogen bonds are established guanosine (FIG. 4) (Leontis et al., 2002). In the crowded space between the Hoogsteen and sugar edges (Walczak), a bulky N6-methyl group can (1) hinder the H-bond formation between N6H of adenosine and 2'OH of guanosine and (2) cause steric clash with the phosphate backbone of guanosine. In this case, while the former has no contribution since both the targets and probes are DNA, the latter can weaken A*-g interaction that results in the differentiation seen in FIG. 2. The dsDNA with an A*-g pair in the middle had a melting temperature lower than that of the dsDNA with an A-g pair (FIG. 5). While testing the same maNCB design (using g as the recognition nucleotide for NC probe) on a second GATC-containing target set29 (Target Set 2 in Table 1), differentiable spectra, similar to those from Target Set 1, were obtained (FIG. 6).

Figure 6A:
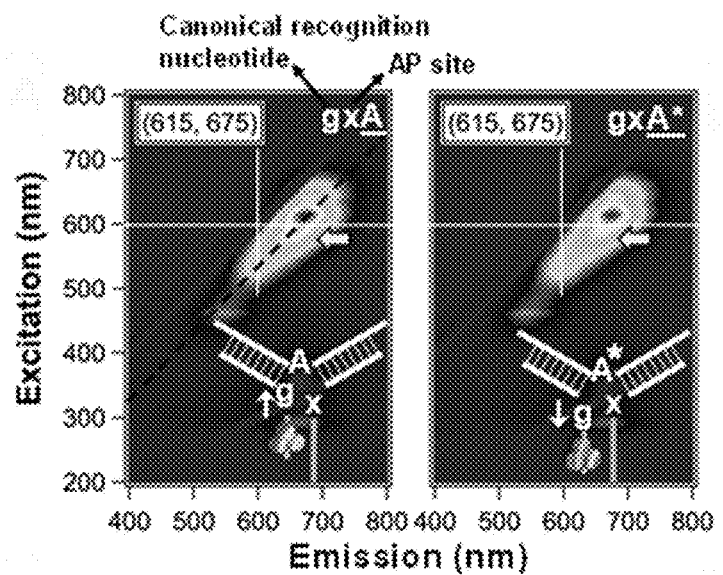
FIGS. 6A-6D: (A) 2D fluorescence contour plots of gxA and gxA* that clearly differentiate between A* and A targets (indicated by thick arrows). The only difference between these two targets (60-nt long) is an A to A* substitution right in the middle of the sequence (Target Set 2 in Table 1). The arrow pointing upwards indicates a stronger A-g interaction as compared to A*-g interaction. (B) Emission profiles of gxA and gxA* (intensity normalized at 670 nm) along the dashed line in A (with Stokes shift of 60 nm). Error bars (represented by ribbons) show standard deviations from five trials. The P value is found to be 0.0008 at 645 nm. (C-D) When using t or a as recognition nucleotides (txA vs. txA* and axA vs. axA*), no significant changes in 2D spectra are observed. Target sequence used here has the GATC motif (Target Set 2).
Figure 6B:
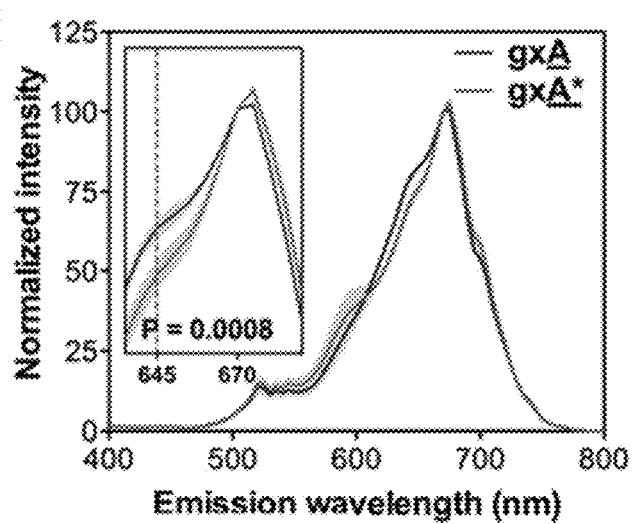
Figure 6C:
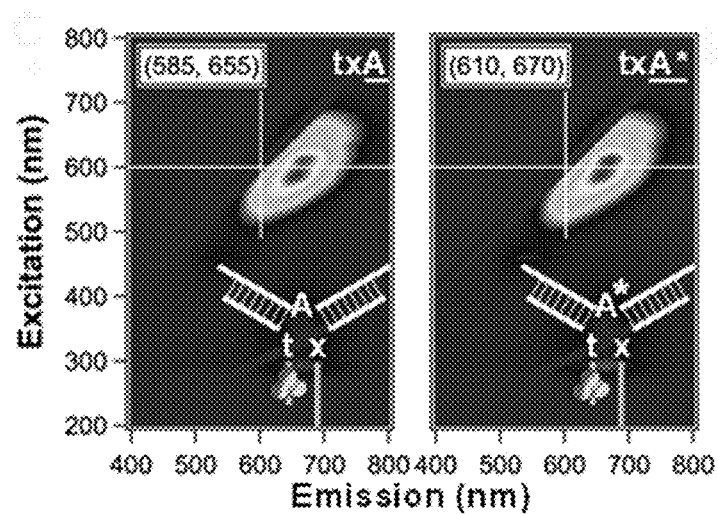
Figure 6D:
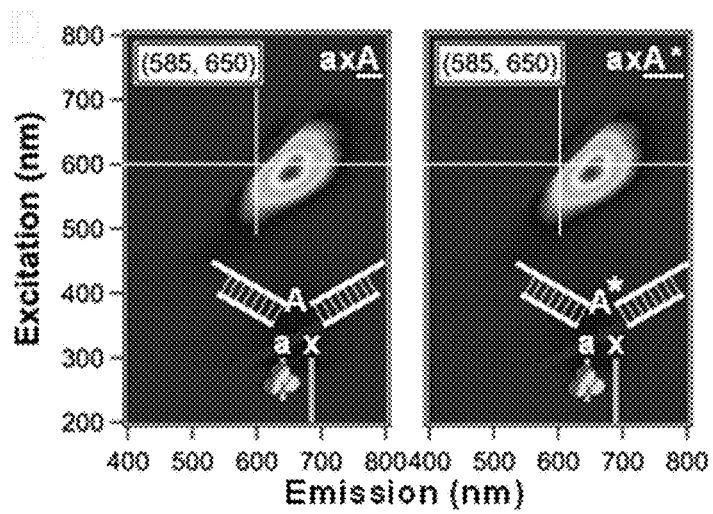
Figure 7A:
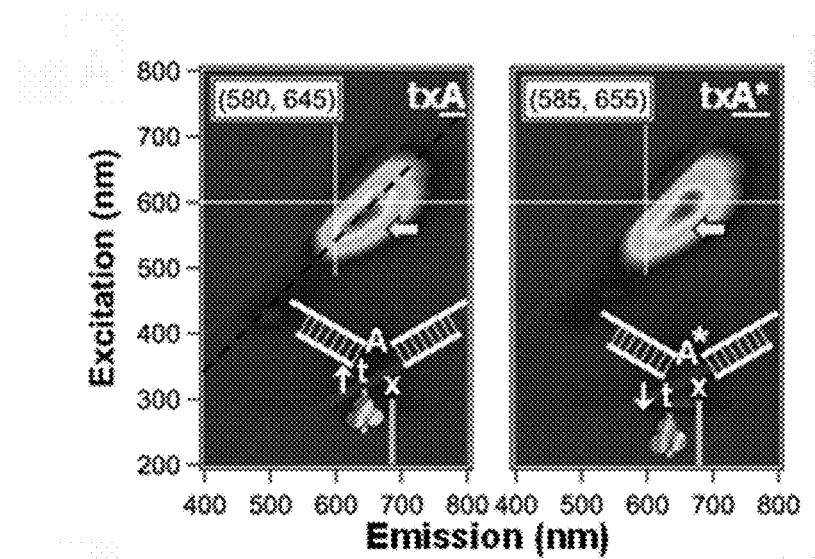
FIGS. 7A-7D: (A) 2D fluorescence contour plots of txA and txA* that clearly differentiate between A* and A targets (indicated by thick arrows). The only difference between these two targets (60-nt long) is an A to A* substitution right in the middle of the sequence (Target Set 3 in Table 2). The arrow pointing upwards indicates a stronger A-t interaction as compared to A*-t interaction. (B) Emission profiles of txA and txA* (intensity normalized at 670 nm) along the black dash line in A (with Stokes shift of 60 nm). Error bars (represented by ribbons) show standard deviations from five trials. The P value is found to be 0.0002 at 620 nm. (C-D) When using g or a as recognition nucleotides (gxA vs. gxA* and axA vs. axA*), no significant changes in 2D spectra are observed. Target sequence used here has the CTGCAG motif (Target Set 3).
Figure 7B:
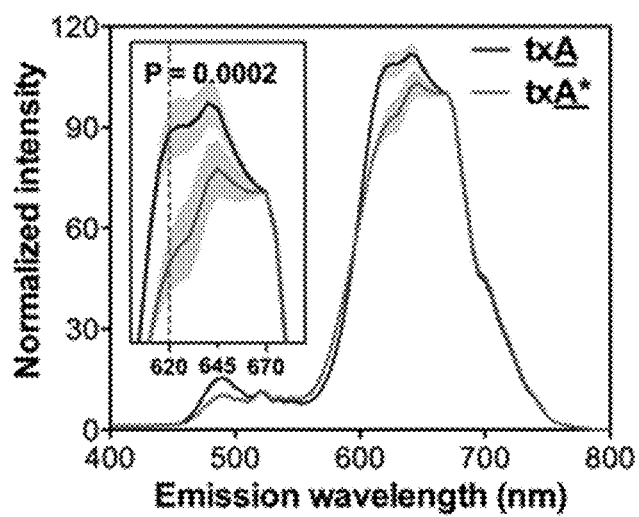
Figure 7C:
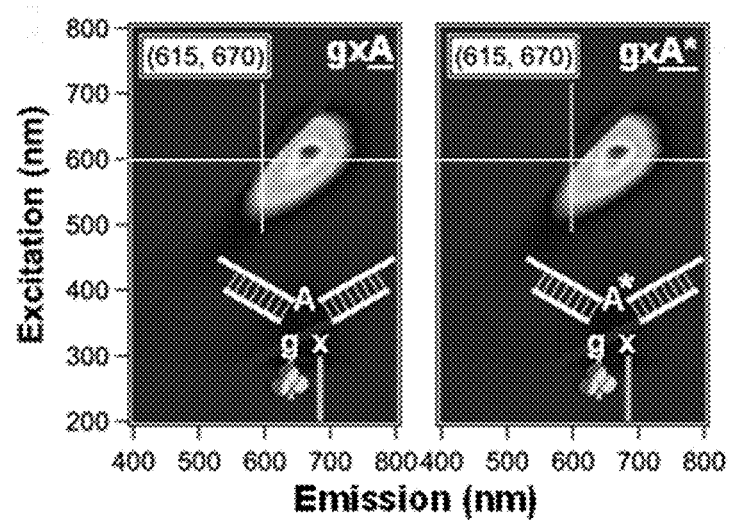
Figure 7D:
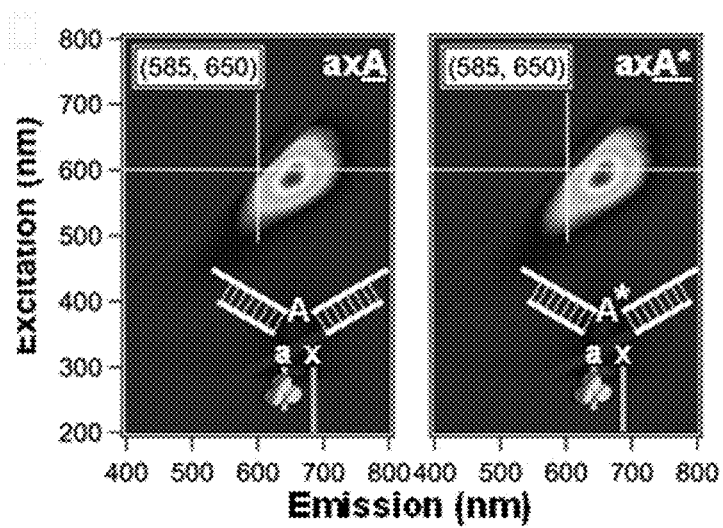
Figure 8A:
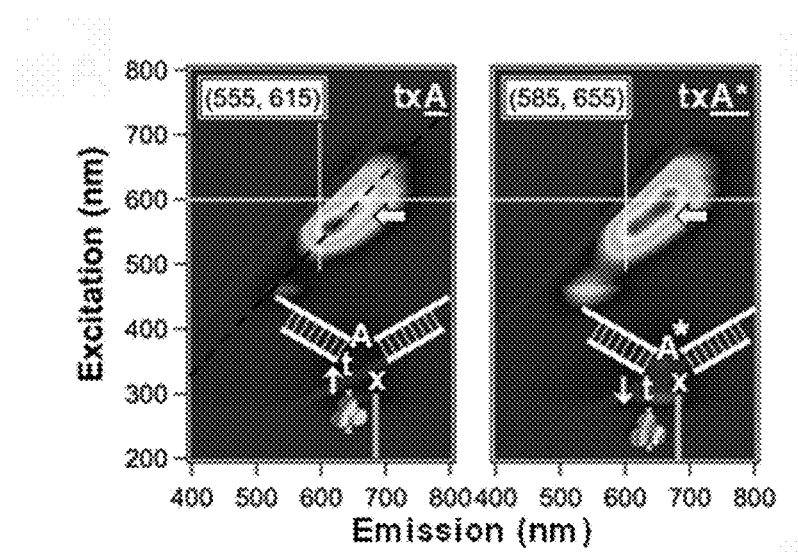
FIGS. 8A-8D: (A) 2D fluorescence contour plots of txA and txA* that clearly differentiate between A* and A targets (indicated by thick arrows). The only difference between these two targets (60-nt long) is an A to A* substitution right in the middle of the sequence (Target Set 4 in Table 2). The arrow pointing upwards indicates a stronger A-t interaction as compared to A*-t interaction. (B) Emission profiles of txA and txA* (intensity normalized at 670 nm) along the dashed line in A (with Stokes shift of 60 nm). Error bars (represented by ribbons) show standard deviations from five trials. The P value is found to be 0.0002 at 620 nm. (C-D) When using g or a as recognition nucleotides (gxA vs. gxA* and axA vs. axA*), no significant changes in 2D spectra are observed. Target sequence used here has the CTGCAG motif (Target Set 4).
Figure 8B:
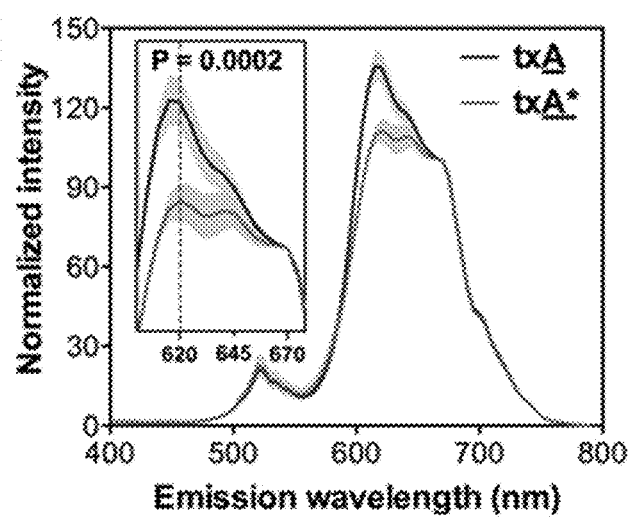
Figure 8C:
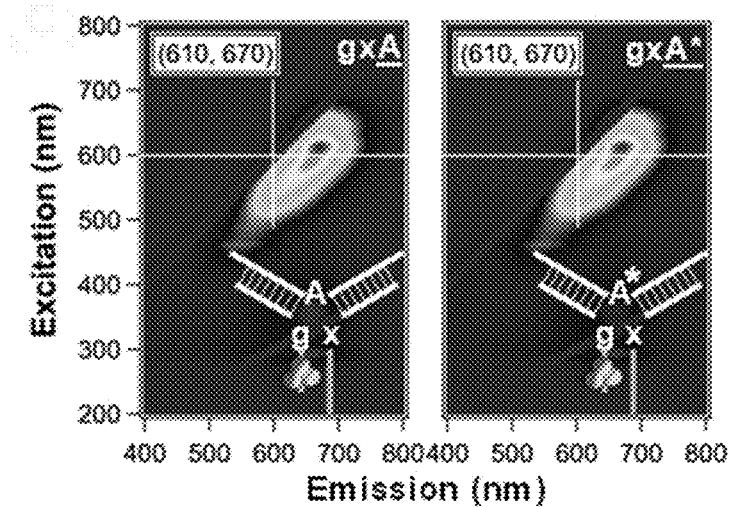
Figure 8D:
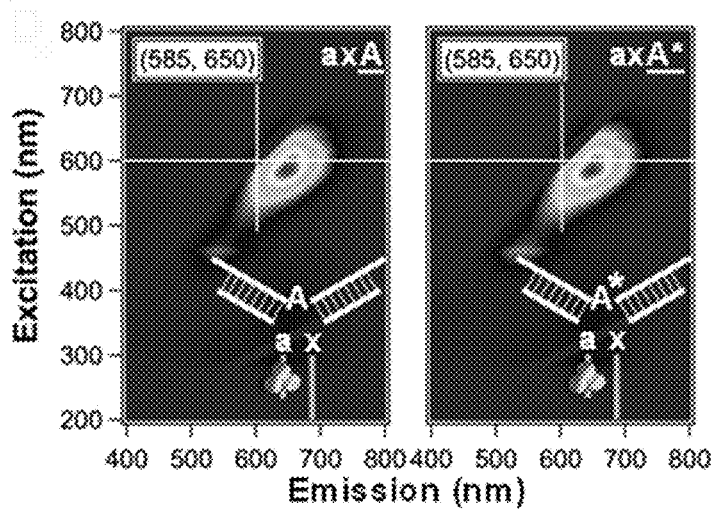

Example 2—Methyladenine-Specific NanoCluster Beacons for CTGCAG-Containing Targets Whereas the first maNCB design worked well for the GATC site, it could not differentiate m6A from A on the CTGCAG site (Target Sets 3 & 4 in Table 2). Instead, t served as a good recognition nucleotide for NC probe to detect m6A on the CTGCAG sites (FIGS. 7 and 8). Upon closer examination, the resulting spectra from the second maNCB design (where t is used as recognition nucleotide) were very different from those obtained from the first maNCB design (where g is used as recognition nucleotide). The gxA and gxA* complexes (from Target Sets 1 & 2) led to two major fluorescent species which emitted at 645 nm and 670 nm, respectively (FIGS. 2B and 6B). Here the differentiation of m6A from A was actually caused by suppression of the 645 nm species relative to the 670 nm species in the gxA* complex. On the other hand, the txA and txA* complexes (from Target Sets 3 & 4) produced at least three major species which emitted at 620 nm, 645 nm, and 670 nm (FIGS. 7B and 8B). The m6A differentiation here was caused by suppression of the 620 nm species relative to the 670 nm species in the txA* complex. While it is not clear why there were two major fluorescent species in one case (with GATC site) and three species in another case (with CTGCAG site), it is obvious that subtle changes in the ligand environment favor the formation of one cluster species over another, enabling the m6A detection through a simple "two-color analysis". In the maNCB detection, the 670 nm emission served as the normalization standard (FIGS. 2B, 6B, 7B and 8B) while the relative intensity at 645 nm (Target Sets 1 & 2) or 620 nm (Target Sets 3 & 4) could differentiate m6A from A. Thus, these maNCB detection results were highly reproducible and consistent among targets ($P \ll 0.05$ in FIGS. 2, 6, 7 and 8).

TABLE 2

Oligonucleotide sequences of maNCBs used for Target Sets 3 and 4.

| Name | DNA Sequence (5'→3') |
|---|---|
| Target Set 3 | |
| Unmethylated target (SEQ ID NO. 15) | CAA TAC ATT ATG GGA AAG TAA TAC AGC TGC AGC GTT TCT GAA CAG AAA GTC ACA GTT TTT |
| Methylated target (SEQ ID NO. 16) | CAA TAC ATT ATG GGA AAG TAA TAC AGC TGC A*GC GTT TCT GAA CAG AAA GTC ACA GTT TTT |
| maNCB_3 | |
| NC probe (SEQ ID NO. 17) | CCC TTA ATC CCC t GCA GCT GTA TTA CTT TCC CAT AAT |
| Enhancer probe (SEQ ID NO. 18) | TGT GAC TTT CTG TTC AGA AAC GCx GGG TGG GGT GGG GTG GGG |

TABLE 2-continued

Oligonucleotide sequences of maNCBs used for Target Sets 3 and 4.

| Name | DNA Sequence (5'→3') |
|---|---|
| Control NC Probes_3 | |
| NC probe_a (SEQ ID NO. 19) | <u>CCC TTA ATC CCC</u> a GCA GCT GTA TTA CTT TCC CAT AAT |
| NC probe_g (SEQ ID NO. 20) | <u>CCC TTA ATC CCC</u> g GCA GCT GTA TTA CTT TCC CAT AAT |
| mNCB_6 | |
| NC probe (SEQ ID NO. 21) | <u>CCC TTA ATC CCC</u> t GTA TTA CTT TCC CAT AAT GTA TTG |
| Enhancer probe (SEQ ID NO. 22) | TTT CTG TTC AGA AAC GCT GCA GCx <u>GGG TGG GGT GGG GTG GGG</u> |
| Target Set 4 | |
| Unmethylated target (SEQ ID NO. 23) | ATC TTG TAA CGC AGC ATC CAG ACG <u>TCC TGC AGC CAG</u> ATC GGA ATA GAC CAA ATC CTG GTT |
| Methylated target (SEQ ID No. 24) | ATC TTG TAA CGC AGC ATC CAG ACG <u>TCC TGC A\*GC CAG</u> ATC GGA ATA GAC CAA ATC CTG GTT |
| maNCB_4 | |
| NC probe (SEQ ID NO. 25) | <u>CCC TTA ATC CCC</u> t GCA GGA CGT CTG GAT GCT GCG TTA |
| Enhancer probe (SEQ ID NO. 26) | GAT TTG GTC TAT TCC GAT CTG GCx <u>GGG TGG GGT GGG GTG GGG</u> |
| Control NC Probes_4 | |
| NC probe_a (SEQ ID NO. 27) | <u>CCC TTA ATC CCC</u> a GCA GGA CGT CTG GAT GCT GCG TTA |
| NC probe_g (SEQ ID NO. 28) | <u>CCC TTA ATC CCC</u> g GCA GGA CGT CTG GAT GCT GCG TTA |

The unmethylated adenine (A) and N⁶-methyladenine (denoted as A\*), the cytosine-rich nucleation sequence, the recognition nucleotide, the hybridization sequence, the abasic site (x) and the G-rich enhancer sequence are shown. Target 3 (Hemday et al., 2002) is related to a papB promoter gene (GenBank: M63747.1; 282..341) while Target 4 (Fang et al., 2013) is associated to a lysine/arginine/ornithine transporter subunit CDS (GenBank: CP010344.1; 2,526,243..2,526,302).

TABLE 3

Oligonucleotide Sequences used for high-resolution melting analysis.

| Name | DNA Sequence (5'→3') |
|---|---|
| Target Set 1 complementary strand | |
| Target Set 1_g (SEQ ID NO. 29) | CCC GAC GCA TGA TCT GTA CTT GAg CGA CCG TGC AAC GCA TGA TCT GTA |
| Target Set 1_t (SEQ ID NO. 30) | CCC GAC GCA TGA TCT GTA CTT GAt CGA CCG TGC AAC GCA TGA TCT GTA |
| Target Set 3 complementary strand | |
| Target Set 3_t (SEQ ID NO. 31) | TGT GAC TTT CTG TTC AGA AAC GCt GCA GCT GTA TTA CTT TCC CAT AAT |

Example 3—Alternate Nucleation Sequences

The nucleation sequence of the nucleation probe can be altered to various lengths. For example, the number of cytosines in the nucleation sequence maNCB were varied in the nucleation probe (Table 4) and found to function similarly. Thus, the number of cytosines can generally be varied to 4, 5, 6, 7, 8, 9, 10, 11, 12, 13, 14, 15 or 16 cytosines.

TABLE 4

Nucleation sequences with various number of cytosines.

| Name | DNA Sequence (5'→3') |
|---|---|
| NC probe (SEQ ID NO. 32) | <u>CC TTA ATC C</u> g CGA CCG TGC AAC GCA TGA TCT GTA |
| NC probe (SEQ ID NO. 33) | <u>CCC TTA ATC CC</u> g CGA CCG TGC AAC GCA TGA TCT GTA |
| NC probe (SEQ ID NO. 34) | <u>CCCC TTA ATC CCC</u> g CGA CCG TGC AAC GCA TGA TCT GTA |
| NC probe (SEQ ID NO. 35) | <u>CCCCC TTA ATC CCCC</u> g CGA CCG TGC AAC GCA TGA TCT GTA |
| NC probe (SEQ ID NO. 36) | <u>CCCCCC TTA ATC CCCCC</u> g CGA CCG TGC AAC GCA TGA TCT GTA |
| NC probe (SEQ ID NO. 37) | <u>CCCCCCC TTA ATC CCCCCC</u> g CGA CCG TGC AAC GCA TGA TCT GTA |
| NC probe (SEQ ID NO. 38) | <u>CCCCCCCC TTA ATC CCCCCCC</u> g CGA CCG TGC AAC GCA TGA TCT GTA |

Example 4—maNCB Quantification and Pinpoint Specificity

Figure 9A:
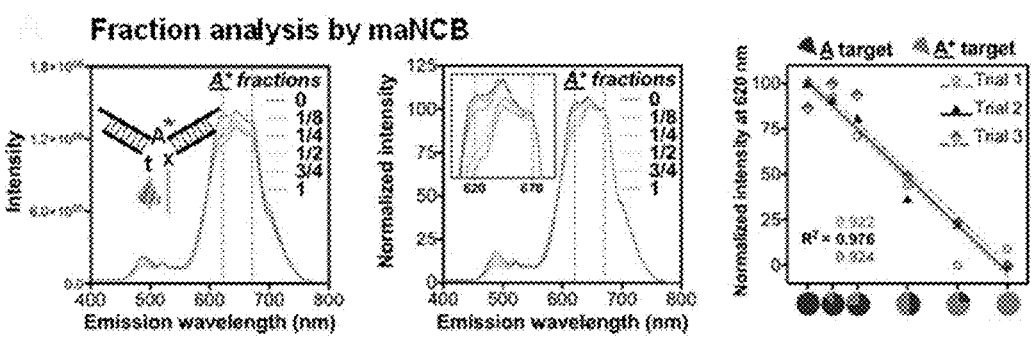
FIGS. 9A-9B: Quantification of adenine methylation extent in heterogeneous samples. (A) Six samples with different A* target fractions (Target Set 3) were prepared and mixed with maNCB_3. Here fraction 0 means 100% A target and fraction 1 means 100% A* target. Fraction 0 has higher intensity and fraction 1 has lower intensity. After normalization at 670 nm, maNCB's emission intensity at 620 nm is found correlated to the amount of A* target in the mixture ($R^2$ range: 0.922 to 0.976). (B) High-resolution melting analysis is also performed in the six dsDNA mixtures. After normalization at 71° C. and 79° C. ($T_m\pm4°$ C.), intercalating dye's emission intensity at 75° C. is also found correlated to the amount of A* target in the mixture ($R^2$=0.984). Target sequence used here has the CTGCAG motif (Target Set 3). The dsDNA used here contains either an A-t or an A*-t base pair in the sequence (Table 3). It was previously shown that A-T pair is more stable than A*-T pair in DNA.
Figure 9B:
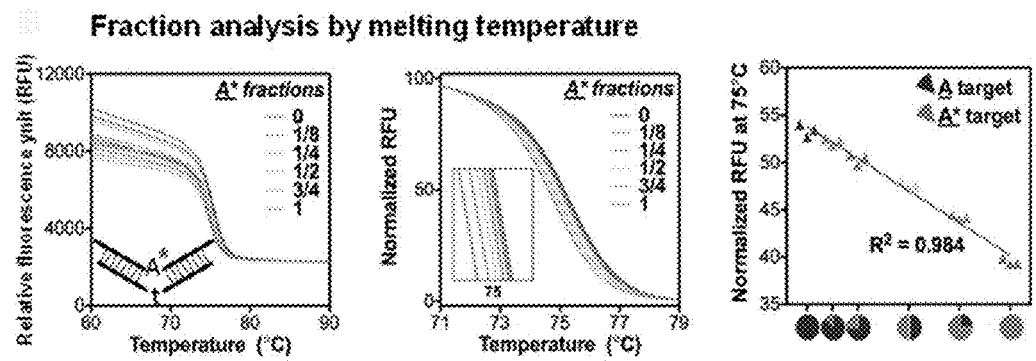
Figure 10A:
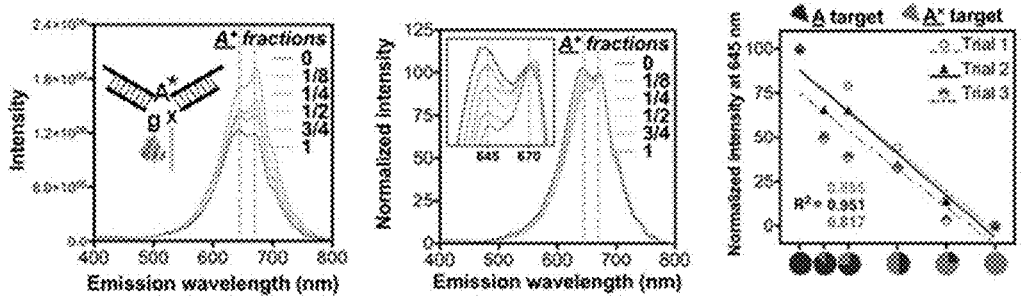
FIGS. 10A-10B: Quantification of adenine methylation extent in heterogeneous samples. (A) Six samples with different A* target fractions (Target Set 1) were prepared and mixed with maNCB_1. Here fraction 0 means 100% A target and fraction 1 means 100% A* target. Fraction 0 has higher intensity and fraction 1 has lower intensity. After normalization at 670 nm, maNCB's emission intensity at 645 nm is found correlated to the amount of A* target in the mixture (R2 range: 0.817 to 0.951). (B) High-resolution melting analysis are also performed in the six dsDNA mixtures. After normalization at 75° C. and 83° C. (Tm±4° C.), intercalating dye's emission intensity at 79° C. was also found correlated to the amount of A* target in the mixture (R2=0.909). Target sequence used here has the GATC motif (Target Set 1). It was previously shown that A-T pair is more stable than A*-T pair in DNA (Lopez et al., 2012).
Figure 10B:
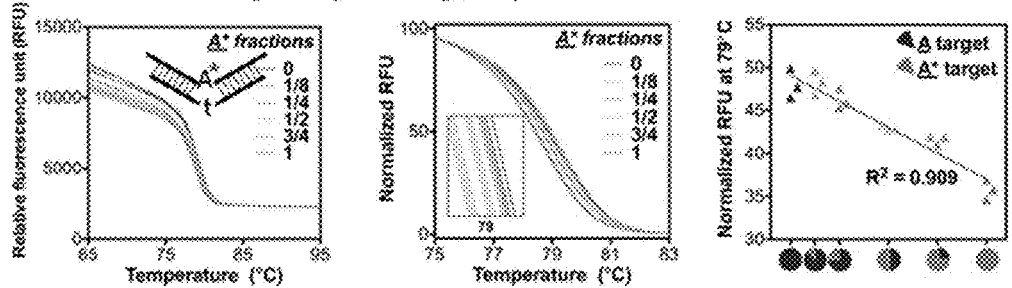

Taking advantage of the large relative-intensity change at 620/645 nm, maNCB can precisely quantify the degree of methylation in heterogeneous samples. Nucleic acid targets are not always fully modified, where incomplete modification can be due to low availability of the co-substrates and limited modification enzyme activities (Saikia et al., 2006). To evaluate maNCB quantification in heterogeneous samples, the A\* and A targets were mixed at six different ratios and compared the resulting relative intensities at a fixed wavelength (645 nm for Target Set 1 in FIG. 10A and 620 nm for Target Set 3 in FIG. 9A). As expected, maNCB's relative emission at 645 nm was found proportional to the A\* target fraction, demonstrating the quantification of methylation degree in heterogeneous samples by maNCB (FIG. 10A). As shown in FIGS. 10B and 9B (see Table 3 for sequences), high-resolution melting (HRM) analysis can also be used for m6A detection (Lopez et al., 20120. Whereas normalized fluorescence intensity of intercalating dye (EvaGreen) also showed a linear trend with A* amount and could be used to quantify the A*/A mixing ratio, the melting analysis cannot "pinpoint" the location of a specific A* modification on the target.

Figure 11:
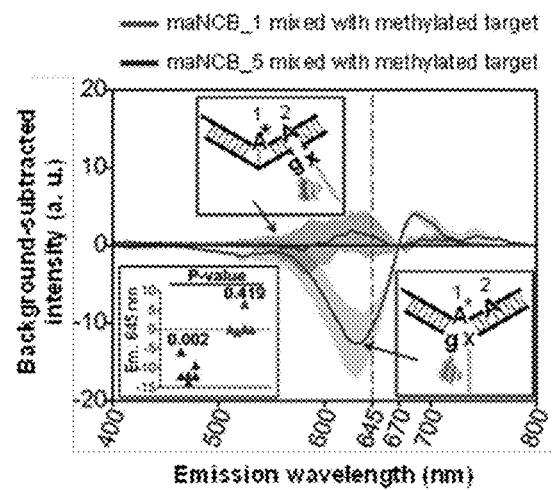
FIG. 11: maNCB can pinpoint the location of a specific $m^6A$ in the DNA sequence. maNCB_1 is designed to target the adenine within the GATC motif (site 1) while maNCB_5 targets a nearby adenine (site 2). Emission spectra from the unmethylated target-probe mixtures are used as background for subtraction. The background-subtracted spectrum of maNCB_5 clearly indicates that maNCB_5 cannot detect $m^6A$ within the GATC motif, while the background-subtracted maNCB_1 spectrum shows an unambiguous detection result of $m^6A$ within the GATC motif at 645 nm (P~0.002). Error bars (represented by ribbons) show standard deviations from five trials.
Figure 12:
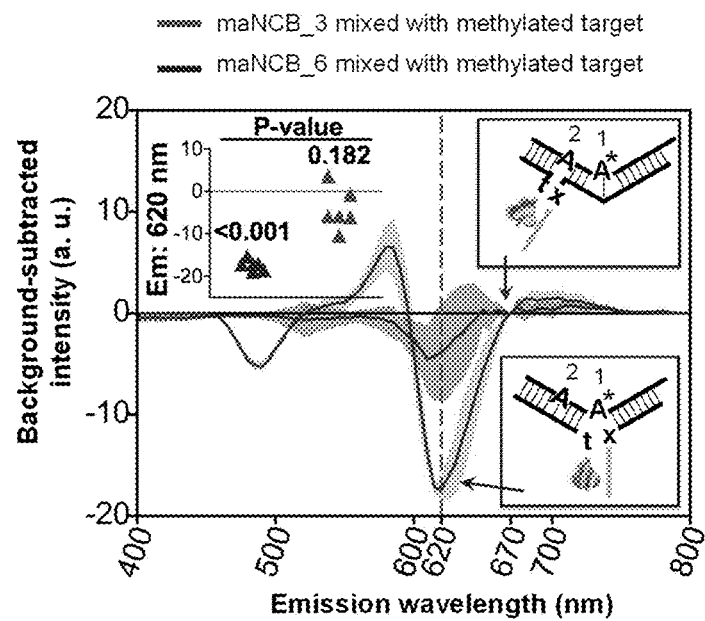
FIG. 12: maNCB can pinpoint the location of a specific $m^6A$ in the DNA sequence. maNCB_3 is designed to target the adenine within the CTGCAG motif (site 1) while maNCB_6 (Table 2) targets a nearby adenine (site 2). Emission spectra from the unmethylated target-probe mixtures are used as background for subtraction. The background-subtracted spectrum of maNCB_6 clearly indicates that maNCB_6 cannot detect $m^6A$ within the CTGCAG motif, while the background-subtracted maNCB_3 spectrum shows an unambiguous detection result of $m^6A$ within the CTGCAG motif at 620 nm (P<0.001). Error bars (represented by ribbons) show standard deviations from five trials.

To demonstrate the capability of maNCB to pinpoint the location of a specific m6A, two maNCBs, which target different adenines in the same target, were designed and tested. As expected, the background-subtracted spectra (FIG. 11) clearly indicated that m6A at site 1 can only be detected by maNCB_1 ($P<<0.05$ at 645 nm), but not maNCB_5 (Table 1). This "pinpoint specificity" in m6A detection was also preserved in the targets with CTGCAG site (FIG. 12 and Table 2).

In summary, the inventors demonstrated the use of maNCBs for m6A detection at the single-base resolution. This enzyme-free detection method comes with high reproducibility and can directly quantify the extent of adenine modification at a particular site in heterogeneous samples. To date, there is no hybridization technique that has the potential to reach these remarkable results. It is expected that the concept of maNCB can be generally applied to the detection of different types of methylation modifications such as 5-methylcytosine (Herman et al., 1996), N4-methylcytosine (Ehrlich et al., 1985), 5-hydroxymethylcytosine (Pfeifer et al., 2013) and N7-methylguanine (Rottman et al., 1974), as long as the suitable recognition nucleotides are identified in the NCB design.

Example 5—Materials and Methods

Sodium phosphate dibasic anhydrous ($Na_2HPO_4$; F.W. 141.96), sodium phosphate monobasic monohydrate ($NaH_2PO_4 \cdot H_2O$; F.W. 137.99), zinc acetate and sodium borohydride ($NaBH_4$) were purchased from Fisher Scientific, Precision Melt Supermix was obtained from Bio-Rad, whereas silver nitrate ($AgNO_3$) was acquired from Sigma-Aldrich. HPLC purified methylated and unmethylated DNA targets were synthesized by TriLink Biotechnologies (San Diego, Calif., USA). All other oligonucleotides were purchased from Integrated DNA Technologies (Coralville, Iowa, USA) and were purified by desalting. De-ionized (DI) water (18 MΩ-cm) was used for all solution preparations.

Preparation of Methyladenine-Specific NanoCluster Beacons (maNCBs)

Preparation of Nanocluster Probes (NC Probes)

In a typical preparation, a 15 μM (final concentration) nanocluster probe (NC probe) solution with a volume of 1 ml was prepared by adding 12.5 μl of 1.2 mM NC probe to 940 μl of 20 mM sodium phosphate buffer (pH 6.7). The solution was vortexed for 2 s and centrifuged at 14,000 rpm for 30 s. 45 μl of 4 mM silver nitrate solution was then added and the mixture was again vortexed and centrifuged. The solution was allowed to sit in the dark for 10 min at room temperature. For silver cluster formation, 7 μl of freshly prepared 13.2 μM $NaBH_4$ solution was added, resulting in a pale yellow mixture which was then stored in the dark overnight. The resulting NC probe solution had the NC probe:$Ag^+$:$NaBH_4$ molar ratio of 1:12:6.

Activation of maNCB

Consisting of an NC probe (i.e. the cytosine-rich Ag cluster-nucleation sequence originally carrying dark silver clusters) and an enhancer probe (i.e. the guanine-rich sequence), maNCB employs a 3-way junction hybridization configuration with a target. When maNCB binds to a target, the enhancer probe is brought close to the NC probe through hybridization and the dark silver clusters are activated and become highly emissive through the interactions with the nearby guanine-rich enhancer sequence. We call this process "the guanine-proximity-induced activation of silver clusters" or, in short, "the activation of maNCBs". To activate maNCBs, 13.3 μl of 0.5 mM zinc acetate was added to a 120 μl aliquot of 10 μM NC probe solution (concentration adjusted from the previously prepared 15 μM NC probe) and the resulting mixture was vortexed. 1 μl of 1.2 mM of an enhancer probe and of a target were added to this mixture, vortexed and immersed in a hot water bath (90-95° C.) for 1 min, followed by gradual cooling to room temperature for 45 min. The activated maNCB had the NC probe:enhancer probe:target molar ratio of 1:1:1.

Fluorescence Measurements

Fluorescence emission and excitation scans were performed on a FluoroMax-4 spectrofluorometer from Horiba Scientific. 120 μl NCB sample was placed in a 100 μl quartz cuvette (16.100F-Q-10/Z15, Starna Cells) for fluorometer measurements. For the 2D measurement, the excitation and emission were scanned from 200 to 800 nm and 400 nm to 800 nm, respectively using 5 nm slit size, 5 nm increment step, and 0.1 s integration time.

High-Resolution Melting Analysis

Single-stranded DNAs were added to the Precision Melt Supermix® (Bio-Rad, USA) to obtain a final DNA concentration of 10 μM. All meltings were performed in 12 μl volumes. The melting curve analysis was conducted on CFX Connect Real-Time System (CFX Manager software version 1.6, Bio-Rad, USA) using the SYBR channel. Before melting, samples were denatured at 93° C. for 1 min and cooled down to room temperature for 30 min. During melting, the temperature was increased from 30 to 100° C. in 0.2° C. incremental steps, with each step held for 2 s. For melting analysis, the relative fluorescence units (RFU) of the resulting melting curves were first plotted against melting temperatures (Tm). Normalization regions were selected before and after the major decrease in fluorescence4 (Tm±4° C.). Comparisons between methylated and unmethylated DNA (fraction analysis) were made in terms of Tm (79° C. for Target Set 1 and 75° C. for Target Set 3).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

US Patent Publication No. 20110212540
US Patent Publication No. 20140349289

Behm-Ansmant, I. et al., Y. *J. Nucleic Acids* 2011.
Cooper, K. K., et al. *BMC Genomics* 2014, 15.
Dai, Q.; Fong, R.; Saikia, M.; Stephenson, D.; Yu, Y.-t.; Pan, T.; Piccirilli, J. A. *Nuc. Acids Res.* 2007, 35, 6322.
Dominissini, D.; Moshitch-Moshkovitz, S.; Salmon-Divon, M.; Amariglio, N.; Rechavi, G. *Nat. Protoc.* 2013, 8, 176.
Ehrlich, M.; Gamasosa, M. A.; Carreira, L. H.; Ljungdahl, L. G.; Kuo, K. C.; Gehrke, C. W. *Nuc. Acids Res.* 1985, 13, 1399.
Fang, G., et al. *Nat. Biotechnol.* 2013, 31, 566.
Flusberg, B. A.; Webster, D. R.; Lee, J. H.; Travers, K. J.; Olivares, E. C.; Clark, T. A.; Korlach, J.; Turner, S. W. *Nat. Methods* 2010, 7, 461.
Harcourt, E. M.; Ehrenschwender, T.; Batista, P. J.; Chang, H. Y.; Kool, E. T. *Journal of the American Chemical Society* 2013, 135, (51), 19079-19082.
Hattman, S. *Biochemistry (Moscow)* 2005, 70, 550.
Herman, J. G.; Graff, J. R.; Myohanen, S.; Nelkin, B. D.; Baylin, S. B. *Proc. Natl. Acad. Sci. USA* 1996, 93, 9821.
Hernday, A.; Krabbe, M.; Braaten, B.; Low, D. *Proc. Natl. Acad. Sci. USA* 2002, 99, 16470.
Juul, S.; Obliosca, J. M.; Liu, C.; Liu, Y.-L.; Chen, Y.-A.; Imphean, D. M.; Knudsen, B. R.; Ho, Y.-P.; Leong, K. W.; Yeh, H.-C. *Nanoscale* 2015, 7, 8332.
Kellner, S.; Burhenne, J.; Helm, M. *RNA Biol.* 2010, 7, 237.
Kolpashchikov, D. M. *Chem. Rev.* 2010, 110, 4709.
Leontis, N. B.; Stombaugh, J.; Westhof, E. *Nuc. Acids Res.* 2002, 30, 3497.
Lopez, C. M.; Lloyd, A. J.; Leonard, K.; Wilkinson, M. J. *Anal. Chem.* 2012, 84, 7336.
Low, D. A.; Weyand, N. J.; Mahan, M. J. *Infect. Immun.* 2001, 69, 7197.
Marinus, M. G. *Annu. Rev. Genet.* 1987, 21, 113.
Marinus, M. G.; Casadesus, J. *FEMS Microbiol. Rev.* 2009, 33, 488.
McCloskey, J. A.; Rozenski, J. *Nuc. Acids Res.* 2005, 33, D135.
Meyer, K. D.; Jaffrey, S. R. *Nature Reviews Molecular Cell Biology* 2014, 15, (5), 313-326.
Obliosca, J. M.; Babin, M. C.; Liu, C.; Liu, Y.-L.; Chen, Y.-A.; Batson, R. A.; Ganguly, M.; Petty, J. T.; Yeh, H.-C. *ACS Nano* 2014, 8, 10150.
Obliosca, J. M.; Liu, C.; Yeh, H.-C. *Nanoscale* 2013, 5, 8443.
Pfeifer, G. P.; Kadam, S.; Jin, S. G. *Epigenet. Chromatin* 2013, 6.
Ratel, D.; Ravanat, J. L.; Berger, F.; Wion, D. *BioEssays* 2006, 28, 309.
Rottman, F.; Shatkin, A. J.; Perry, R. P. *Cell* 1974, 3, 197.
Rozenski, J.; Crain, P. F.; McCloskey, J. A. *Nuc. Acids Res.* 1999, 27, 196.
Saikia, M.; Dai, Q.; Decatur, W. A.; Fournier, M. J.; Piccirilli, J. A.; Pan, T. *RNA* 2006, 12, 2025.
Sharma, J.; Yeh, H.-C.; Yoo, H.; Werner, J. H.; Martinez, J. S. *Chem. Commun.* 2010, 46, 3280.
Song, C.-X.; Yi, C.; He, C. *Nat. Biotechnol.* 2012, 30, 1107.
Vanyushin, B.; Alexandrushkina, N.; Kirnos, M. *FEBS Lett.* 1988, 233, 397.
Walczak, R.; Carbon, P.; Krol, A. *RNA* 1998, 4, 74.
Wion, D.; Casadesús, J. *Nat. Rev. Microbiol.* 2006, 4, 183.
Yeh, H.-C.; Sharma, J.; Han, J. J.; Martinez, J. S.; Werner, J. H. *Nano Lett.* 2010, 10, 3106.
Yeh, H.-C.; Sharma, J.; Han, J. J.; Martinez, J. S.; Werner, J. H. *IEEE Nanotechnol. Mag.* 2011, 5, 28.
Yeh, H.-C.; Sharma, J.; Shih Ie, M.; Vu, D. M.; Martinez, J. S.; Werner, J. H. *J. Am. Chem. Soc.* 2012, 134, 11550.

---

What is claimed is:

1. A method for detecting an epigenetic modification in a test nucleic acid sample comprising:
   (I) hybridizing the test nucleic acid sample to a first and second probe, wherein
      (a) the first probe comprises (i) a hybridization sequence that is complementary to a first sequence in the test nucleic acid sample; (ii) an abasic site or a recognition nucleotide that interacts with the nucleotide that comprises the epigenetic modification in the test nucleic acid; and (iii) a nucleation sequence comprising a fluorescent metal nanocluster; and
      (b) the second probe comprises (iv) an enhancer sequence that enhances fluorescence of the fluorescent metal nanocluster when the enhancer sequence interacts with the nucleation sequence of the first probe; (v) an abasic site or a recognition nucleotide that interacts with the nucleotide that comprises the epigenetic modification in the test nucleic acid; and (vi) a hybridization sequence that is complementary to a second sequence in the test nucleic acid sample;
      wherein if the first probe comprises a recognition nucleotide then the second probe comprises an abasic site;
      wherein if the first probe comprises an abasic site then the second probe comprises a recognition nucleotide;
   (II) exposing the test nucleic acid sample and the first and second probes to an excitation light; and
   (III) detecting a fluorescence signal from the fluorescent metal nanocluster, thereby detecting an epigenetic modification in the test nucleic acid sample.

2. The method of claim 1, wherein step (I) comprises hybridizing the test nucleic acid sample to a first and second probe, wherein
   (a) the first probe comprises (i) a hybridization sequence that is complementary to a first sequence in the test nucleic acid sample; (ii) a recognition nucleotide that interacts with the nucleotide that comprises the epigenetic modification in the test nucleic acid; and (iii) a nucleation sequence comprising a fluorescent metal nanocluster; and
   (b) the second probe comprises (iv) an enhancer sequence that enhances fluorescence of the fluorescent metal nanocluster when the enhancer sequence interacts with the nucleation sequence of the first probe; (v) an abasic site; and (vi) a hybridization sequence that is complementary to a second sequence in the test nucleic acid sample.

3. The method of claim 1, wherein step (I) comprises hybridizing the test nucleic acid sample to a first and second probe, wherein
   (a) the first probe comprises (i) a hybridization sequence that is complementary to a first sequence in the test nucleic acid sample; (ii) an abasic site; and (iii) a nucleation sequence comprising a fluorescent metal nanocluster; and
   (b) the second probe comprises (iv) an enhancer sequence that enhances fluorescence of the fluorescent metal nanocluster when the enhancer sequence interacts with the nucleation sequence of the first probe; (v) a recognition nucleotide that interacts with the nucleotide that comprises the epigenetic modification in the test nucleic acid; and (vi) a hybridization sequence that is complementary to a second sequence in the test nucleic acid sample.

4. The method of claim 1, wherein the first sequence in the nucleic acid sample is positioned 5' relative to the second sequence of the nucleic acid sample.

5. The method of claim 1, wherein the first sequence in the nucleic acid sample and the second sequence of the nucleic acid sample are separated by one nucleotide, which is a candidate nucleotide.

6. The method of claim 1, wherein (III) detecting the fluorescence signal from the fluorescent metal nanocluster comprises detecting a change in the fluorescence signal detected in the test nucleic acid sample as compared to a control nucleic acid sample.

7. The method of claim 6, wherein the change in the fluorescence signal is a change in the wavelength of the fluorescence signal.

8. The method of claim 7, wherein the change in the fluorescence signal is a change of at least 1 nm in the wavelength of the fluorescence signal.

9. The method of claim 6, wherein the control nucleic acid sample comprises nucleic acid molecules that are known to include the epigenetic modification.

10. The method of claim 6, wherein the control nucleic acid sample comprises nucleic acid molecules that are known not to include the epigenetic modification.

11. The method of claim 1, wherein detecting the fluorescence signal from the fluorescent metal nanocluster further comprises quantifying the fluorescence signal from the fluorescent metal nanocluster, thereby quantifying the proportion of nucleic acid molecules in the sample that comprise the epigenetic modification.

12. The method of claim 11, wherein quantifying the fluorescence signal from the fluorescent metal nanocluster comprises quantifying a change in the fluorescence signal detected in the test nucleic acid sample as compared to a control nucleic acid sample.

13. The method of claim 1, wherein the epigenetic modification is selected from the group consisting of 5-methylcytosine, $N^4$-methylcytosine, 5-hydroxymethylcytosine, $N^7$-methylguanosine and $N^6$-methyladenine.

14. The method of claim 1, wherein the epigenetic modification is $N^6$-methyladenine.

* * * * *

SEQUENCE LISTING

```
<160> NUMBER OF SEQ ID NOS: 38

<210> SEQ ID NO 1
<211> LENGTH: 60
<212> TYPE: DNA
<213> ORGANISM: Artificial Sequence
<220> FEATURE:
<223> OTHER INFORMATION: Target Set 1 Unmethylated target

<400> SEQUENCE: 1
atcaagtaca gatcatgcgt tgcacggtcg atcaagtaca gatcatgcgt cgggctcgga        60

<210> SEQ ID NO 2
<211> LENGTH: 60
<212> TYPE: DNA
<213> ORGANISM: Artificial Sequence
<220> FEATURE:
<223> OTHER INFORMATION: Target Set 1 methylated target

<400> SEQUENCE: 2
atcaagtaca gatcatgcgt tgcacggtcg atcaagtaca gatcatgcgt cgggctcgga        60

<210> SEQ ID NO 3
<211> LENGTH: 37
<212> TYPE: DNA
<213> ORGANISM: Artificial Sequence
<220> FEATURE:
<223> OTHER INFORMATION: maNCB_1 NC probe

<400> SEQUENCE: 3
cccttaatcc ccgcgaccgt gcaacgcatg atctgta        37
```

<210> SEQ ID NO 4
<211> LENGTH: 41
<212> TYPE: DNA
<213> ORGANISM: Artificial Sequence
<220> FEATURE:
<223> OTHER INFORMATION: maNCB_1 Enhancer probe

<400> SEQUENCE: 4
cccgacgcat gatctgtact tgagggtggg gtggggtggg g                 41

<210> SEQ ID NO 5
<211> LENGTH: 37
<212> TYPE: DNA
<213> ORGANISM: Artificial Sequence
<220> FEATURE:
<223> OTHER INFORMATION: Control NC Probe_a 1

<400> SEQUENCE: 5
cccttaatcc ccacgaccgt gcaacgcatg atctgta                      37

<210> SEQ ID NO 6
<211> LENGTH: 37
<212> TYPE: DNA
<213> ORGANISM: Artificial Sequence
<220> FEATURE:
<223> OTHER INFORMATION: NC Probe_t 1

<400> SEQUENCE: 6
cccttaatcc cctcgaccgt gcaacgcatg atctgta                      37

<210> SEQ ID NO 7
<211> LENGTH: 37
<212> TYPE: DNA
<213> ORGANISM: Artificial Sequence
<220> FEATURE:
<223> OTHER INFORMATION: maNCB_5 NC probe

<400> SEQUENCE: 7
cccttaatcc ccgacttgat cgaccgtgca acgcatg                      37

<210> SEQ ID NO 8
<211> LENGTH: 40
<212> TYPE: DNA
<213> ORGANISM: Artificial Sequence
<220> FEATURE:
<223> OTHER INFORMATION: maNCB_5 enhancer probe

<400> SEQUENCE: 8
tccgagcccg acgcatgatc tggggtgggg tggggtgggg                   40

<210> SEQ ID NO 9
<211> LENGTH: 60
<212> TYPE: DNA
<213> ORGANISM: Artificial Sequence
<220> FEATURE:
<223> OTHER INFORMATION: Target set 2 unmethylated target

<400> SEQUENCE: 9
ctagtttaat tttgttttgt gggttaaaag atcgtttaaa tcaatattta caacataaaa    60

<210> SEQ ID NO 10
<211> LENGTH: 60
<212> TYPE: DNA
<213> ORGANISM: Artificial Sequence
<220> FEATURE:

<223> OTHER INFORMATION: Target Set 2 unmethylated target

<400> SEQUENCE: 10
ctagtttaat tttgttttgt gggttaaaag atcgtttaaa tcaatattta caacataaaa     60

<210> SEQ ID NO 11
<211> LENGTH: 37
<212> TYPE: DNA
<213> ORGANISM: Artificial Sequence
<220> FEATURE:
<223> OTHER INFORMATION: maNCB_2 NC probe

<400> SEQUENCE: 11
cccttaatcc ccgcttttaa cccacaaaac aaaatta                              37

<210> SEQ ID NO 12
<211> LENGTH: 41
<212> TYPE: DNA
<213> ORGANISM: Artificial Sequence
<220> FEATURE:
<223> OTHER INFORMATION: maNCB_2 Enhancer probe

<400> SEQUENCE: 12
gttgtaaata ttgatttaaa cgagggtggg gtggggtggg g                         41

<210> SEQ ID NO 13
<211> LENGTH: 37
<212> TYPE: DNA
<213> ORGANISM: Artificial Sequence
<220> FEATURE:
<223> OTHER INFORMATION: Control NC probe_a 2

<400> SEQUENCE: 13
cccttaatcc ccacttttaa cccacaaaac aaaatta                              37

<210> SEQ ID NO 14
<211> LENGTH: 37
<212> TYPE: DNA
<213> ORGANISM: Artificial Sequence
<220> FEATURE:
<223> OTHER INFORMATION: Control NC probe_t 2

<400> SEQUENCE: 14
cccttaatcc cctcttttaa cccacaaaac aaaatta                              37

<210> SEQ ID NO 15
<211> LENGTH: 60
<212> TYPE: DNA
<213> ORGANISM: Artificial Sequence
<220> FEATURE:
<223> OTHER INFORMATION: Target Set 3 Unmethylated target

<400> SEQUENCE: 15
caatacatta tgggaaagta atacagctgc agcgtttctg aacagaaagt cacagttttt     60

<210> SEQ ID NO 16
<211> LENGTH: 60
<212> TYPE: DNA
<213> ORGANISM: Artificial Sequence
<220> FEATURE:
<223> OTHER INFORMATION: Target Set 3 methylated target

<400> SEQUENCE: 16
caatacatta tgggaaagta atacagctgc agcgtttctg aacagaaagt cacagttttt     60

```
<210> SEQ ID NO 17
<211> LENGTH: 37
<212> TYPE: DNA
<213> ORGANISM: Artificial Sequence
<220> FEATURE:
<223> OTHER INFORMATION: maNCB_3 NC probe

<400> SEQUENCE: 17
cccttaatcc cctgcagctg tattactttc ccataat                              37

<210> SEQ ID NO 18
<211> LENGTH: 41
<212> TYPE: DNA
<213> ORGANISM: Artificial Sequence
<220> FEATURE:
<223> OTHER INFORMATION: maNCB_3 Enhancer probe

<400> SEQUENCE: 18
tgtgactttc tgttcagaaa cgcgggtggg gtggggtggg g                         41

<210> SEQ ID NO 19
<211> LENGTH: 37
<212> TYPE: DNA
<213> ORGANISM: Artificial Sequence
<220> FEATURE:
<223> OTHER INFORMATION: Control NC Probe_a 3

<400> SEQUENCE: 19
cccttaatcc ccagcagctg tattactttc ccataat                              37

<210> SEQ ID NO 20
<211> LENGTH: 37
<212> TYPE: DNA
<213> ORGANISM: Artificial Sequence
<220> FEATURE:
<223> OTHER INFORMATION: Control NC Probe_g 3

<400> SEQUENCE: 20
cccttaatcc ccggcagctg tattactttc ccataat                              37

<210> SEQ ID NO 21
<211> LENGTH: 37
<212> TYPE: DNA
<213> ORGANISM: Artificial Sequence
<220> FEATURE:
<223> OTHER INFORMATION: maNCB_6 NC probe

<400> SEQUENCE: 21
cccttaatcc cctgtattac tttcccataa tgtattg                              37

<210> SEQ ID NO 22
<211> LENGTH: 41
<212> TYPE: DNA
<213> ORGANISM: Artificial Sequence
<220> FEATURE:
<223> OTHER INFORMATION: maNCB_6 Enhancer probe

<400> SEQUENCE: 22
tttctgttca gaaacgctgc agcgggtggg gtggggtggg g                         41

<210> SEQ ID NO 23
<211> LENGTH: 60
<212> TYPE: DNA
<213> ORGANISM: Artificial Sequence
<220> FEATURE:
<223> OTHER INFORMATION: Target Set 4 Unmethylated target
```

<400> SEQUENCE: 23
atcttgtaac gcagcatcca gacgtcctgc agccagatcg aatagacca aatcctggtt    60

<210> SEQ ID NO 24
<211> LENGTH: 60
<212> TYPE: DNA
<213> ORGANISM: Artificial Sequence
<220> FEATURE:
<223> OTHER INFORMATION: Target Set 4 Methylated Target

<400> SEQUENCE: 24
atcttgtaac gcagcatcca gacgtcctgc agccagatcg aatagacca aatcctggtt    60

<210> SEQ ID NO 25
<211> LENGTH: 37
<212> TYPE: DNA
<213> ORGANISM: Artificial Sequence
<220> FEATURE:
<223> OTHER INFORMATION: maNCB_4 NC probe

<400> SEQUENCE: 25
cccttaatcc cctgcaggac gtctggatgc tgcgtta    37

<210> SEQ ID NO 26
<211> LENGTH: 41
<212> TYPE: DNA
<213> ORGANISM: Artificial Sequence
<220> FEATURE:
<223> OTHER INFORMATION: maNCB_4 Enhancer probe

<400> SEQUENCE: 26
gatttggtct attccgatct ggcgggtggg gtggggtggg g    41

<210> SEQ ID NO 27
<211> LENGTH: 37
<212> TYPE: DNA
<213> ORGANISM: Artificial Sequence
<220> FEATURE:
<223> OTHER INFORMATION: NC probe_a 4

<400> SEQUENCE: 27
cccttaatcc ccagcaggac gtctggatgc tgcgtta    37

<210> SEQ ID NO 28
<211> LENGTH: 37
<212> TYPE: DNA
<213> ORGANISM: Artificial Sequence
<220> FEATURE:
<223> OTHER INFORMATION: Control NC Probe_g 4

<400> SEQUENCE: 28
cccttaatcc ccggcaggac gtctggatgc tgcgtta    37

<210> SEQ ID NO 29
<211> LENGTH: 48
<212> TYPE: DNA
<213> ORGANISM: Artificial Sequence
<220> FEATURE:
<223> OTHER INFORMATION: Target Set 1_g complementary strand

<400> SEQUENCE: 29
cccgacgcat gatctgtact tgagcgaccg tgcaacgcat gatctgta    48

<210> SEQ ID NO 30
<211> LENGTH: 48

<212> TYPE: DNA
<213> ORGANISM: Artificial Sequence
<220> FEATURE:
<223> OTHER INFORMATION: Target Set 1_t complementary strand

<400> SEQUENCE: 30
cccgacgcat gatctgtact tgatcgaccg tgcaacgcat gatctgta        48

<210> SEQ ID NO 31
<211> LENGTH: 48
<212> TYPE: DNA
<213> ORGANISM: Artificial Sequence
<220> FEATURE:
<223> OTHER INFORMATION: Target Set 3 complementary strand

<400> SEQUENCE: 31
tgtgactttc tgttcagaaa cgctgcagct gtattacttt cccataat        48

<210> SEQ ID NO 32
<211> LENGTH: 34
<212> TYPE: DNA
<213> ORGANISM: Artificial Sequence
<220> FEATURE:
<223> OTHER INFORMATION: NC probe 4C

<400> SEQUENCE: 32
ccttaatccg cgaccgtgca acgcatgatc tgta        34

<210> SEQ ID NO 33
<211> LENGTH: 36
<212> TYPE: DNA
<213> ORGANISM: Artificial Sequence
<220> FEATURE:
<223> OTHER INFORMATION: NC probe 6C

<400> SEQUENCE: 33
cccttaatcc cgcgaccgtg caacgcatga tctgta        36

<210> SEQ ID NO 34
<211> LENGTH: 38
<212> TYPE: DNA
<213> ORGANISM: Artificial Sequence
<220> FEATURE:
<223> OTHER INFORMATION: NC probe 8C

<400> SEQUENCE: 34
ccccttaatc cccgcgaccg tgcaacgcat gatctgta        38

<210> SEQ ID NO 35
<211> LENGTH: 40
<212> TYPE: DNA
<213> ORGANISM: Artificial Sequence
<220> FEATURE:
<223> OTHER INFORMATION: NC probe 10C

<400> SEQUENCE: 35
cccccttaat ccccgcgac cgtgcaacgc atgatctgta        40

<210> SEQ ID NO 36
<211> LENGTH: 42
<212> TYPE: DNA
<213> ORGANISM: Artificial Sequence
<220> FEATURE:
<223> OTHER INFORMATION: NC probe 10C

<400> SEQUENCE: 36

```
ccccccttaa tcccccgcg accgtgcaac gcatgatctg ta          42

<210> SEQ ID NO 37
<211> LENGTH: 44
<212> TYPE: DNA
<213> ORGANISM: Artificial Sequence
<220> FEATURE:
<223> OTHER INFORMATION: NC probe 14C

<400> SEQUENCE: 37
ccccccctta atcccccccg cgaccgtgca acgcatgatc tgta       44

<210> SEQ ID NO 38
<211> LENGTH: 46
<212> TYPE: DNA
<213> ORGANISM: Artificial Sequence
<220> FEATURE:
<223> OTHER INFORMATION: NC probe 16C

<400> SEQUENCE: 38
cccccccctt aatccccccc cgcgaccgtg caacgcatga tctgta     46
```